US012752032B2

(12) United States Patent
Gauthier et al.

(10) Patent No.: US 12,752,032 B2
(45) Date of Patent: Oct. 6, 2026

(54) MULTI-COMPONENT VARIABLE CONTROL FRAGRANCE DISPENSING SYSTEM APPARATUS

(71) Applicant: Creative Elements NY LLC, New York, NY (US)

(72) Inventors: Monique Rene Gauthier, Long Island City, NY (US); Ryon Mathew Smey, Long Island City, NY (US)

(73) Assignee: Creative Elements NY LLC, New York, NY (US)

( * ) Notice: Subject to any disclaimer, the term of this patent is extended or adjusted under 35 U.S.C. 154(b) by 216 days.

(21) Appl. No.: 18/519,949

(22) Filed: Nov. 27, 2023

(65) Prior Publication Data

US 2024/0091398 A1 Mar. 21, 2024

Related U.S. Application Data

(63) Continuation-in-part of application No. 17/366,693, filed on Jul. 2, 2021, now Pat. No. 11,833,535.

(Continued)

(51) Int. Cl.

*A61L 9/14* (2006.01)
*B05B 7/04* (2006.01)

(Continued)

(52) U.S. Cl.

CPC .............. *A61L 9/14* (2013.01); *B05B 7/0408* (2013.01); *B05B 7/1209* (2013.01); *B05B 11/0054* (2013.01); *B05B 11/0081* (2013.01); *B05B 11/0089* (2013.01); *B05B 11/1083* (2023.01); *B05B 12/002* (2013.01);

(Continued)

(58) Field of Classification Search

CPC .. A61L 9/14; A61L 2209/11; A61L 2209/133; A61L 2209/134; B05B 11/0081; B05B 11/0089; B05B 12/002; B05B 7/1209; B05B 11/06; B05B 12/00; B05B 7/0408; B05B 11/0054; B05B 11/1083; B05B 12/1409

See application file for complete search history.

(56) References Cited

U.S. PATENT DOCUMENTS 4,355,739 A 10/1982 Vierkoetter
5,152,461 A * 10/1992 Proctor ............... B05B 11/0064 239/304

(Continued)

OTHER PUBLICATIONS

More is MORE Perfume for Her by Judith Leiber, https://shop.judithleibermoreismore.com/products/more-is-more- perfume-women (retrieved Feb. 25, 2021).

(Continued)

*Primary Examiner* — Frederick C Nicolas
(74) *Attorney, Agent, or Firm* — Wang Hardoon, P.C.

(57) ABSTRACT

Apparatus and methods for variable-control fragrance dispensing. The disclosed device brings customization to the fragrance industry. Interchanging sub-containers and selecting the amounts of each sub-container allows a user to customize their scents. A mixing chamber contained to receive and mix a variable amount of each liquid from a plurality of sub-containers is described. The mixed liquid is sprayable out a spray head of the device. Selector knobs may be used to control valves which control the variable amount of each liquid dispensed.

18 Claims, 13 Drawing Sheets

Related U.S. Application Data

(60) Provisional application No. 62/705,916, filed on Jul. 22, 2020.

(51) Int. Cl.

| | |
|---|---|
| ***B05B 7/12*** | (2006.01) |
| ***B05B 11/00*** | (2023.01) |
| ***B05B 11/10*** | (2023.01) |
| ***B05B 12/00*** | (2018.01) |
| ***B05B 12/14*** | (2006.01) |
| *B05B 11/06* | (2006.01) |

(52) U.S. Cl.

CPC ....... *B05B 12/1409* (2013.01); *A61L 2209/11* (2013.01); *A61L 2209/133* (2013.01); *A61L 2209/134* (2013.01); *B05B 11/06* (2013.01); *B05B 12/00* (2013.01)

(56) References Cited

U.S. PATENT DOCUMENTS

| | | | | |
|---|---|---|---|---|
| 5,848,732 | A | 12/1998 | Brugger | |
| 8,596,498 | B2 * | 12/2013 | Werner | B05B 11/1083 222/145.5 |
| 11,833,535 | B2 * | 12/2023 | Gauthier | B01F 33/50111 |
| 2004/0159677 | A1 | 8/2004 | Hwang | |
| 2012/0279990 | A1 | 11/2012 | Werner et al. | |
| 2017/0239675 | A1 * | 8/2017 | Svendsen | B05B 12/002 |
| 2020/0178671 | A1 | 6/2020 | Edwards | |
| 2021/0188614 | A1 | 6/2021 | Labarbera et al. | |
| 2021/0199483 | A1 | 7/2021 | Fyfe | |
| 2022/0161283 | A1 * | 5/2022 | Michalicek | A61L 2/18 |

OTHER PUBLICATIONS

NINU Perfume Reinvented, https://ninuperfume.com (retrieved Mar. 8, 2021).

* cited by examiner

FIG 3
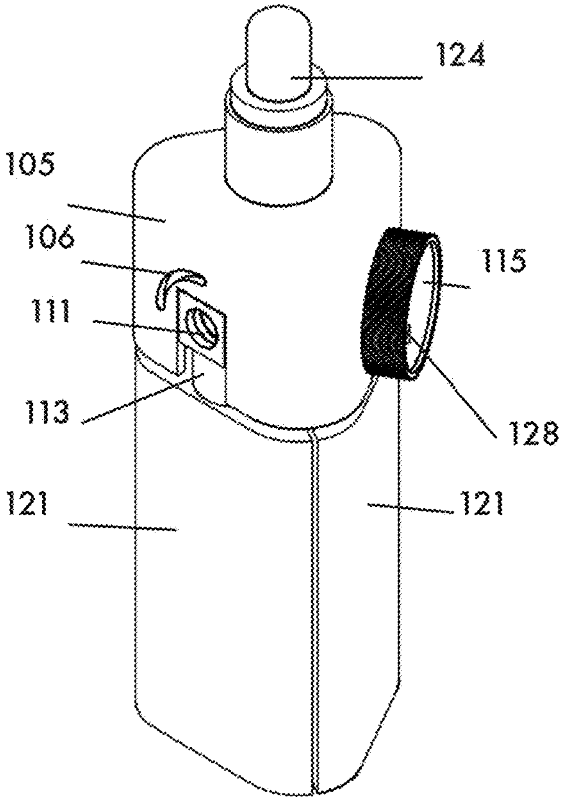
FIG 3A
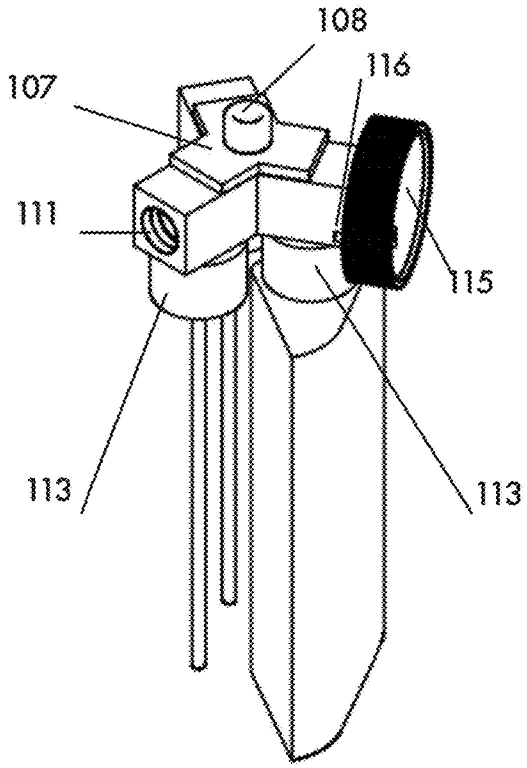
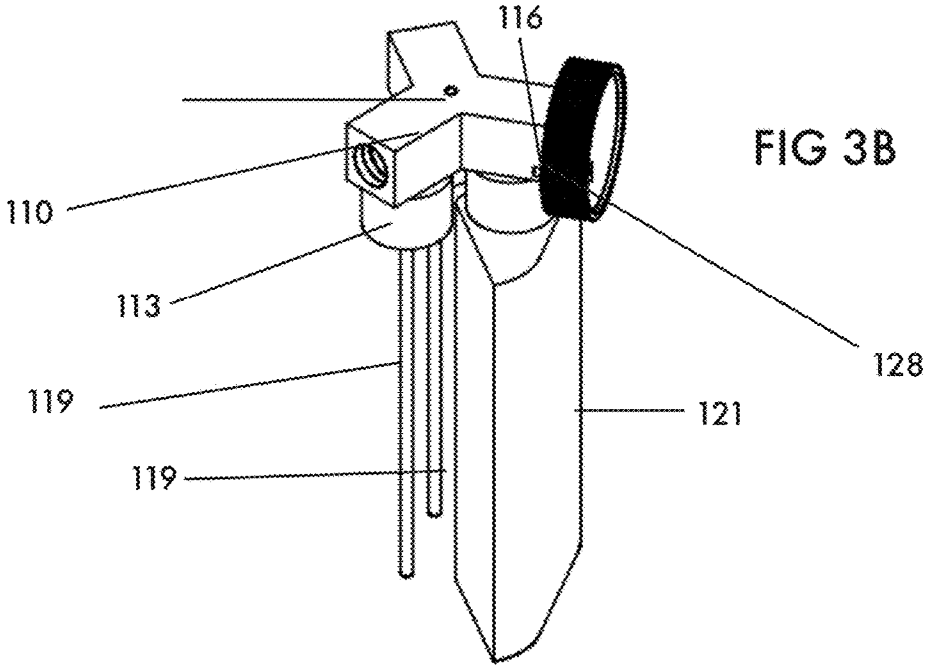
FIG 3B

A-A (1:1)

FIG 8
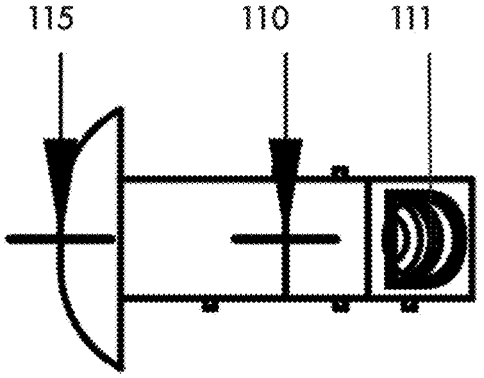
FIG 8A
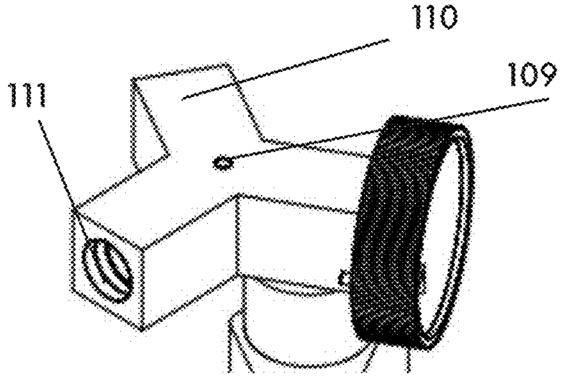
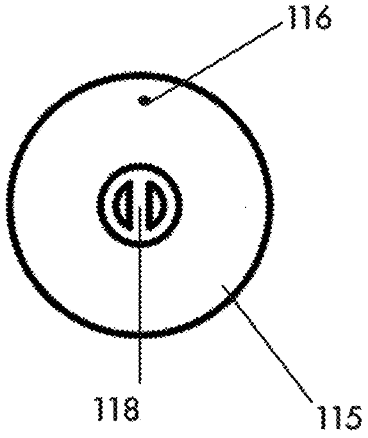
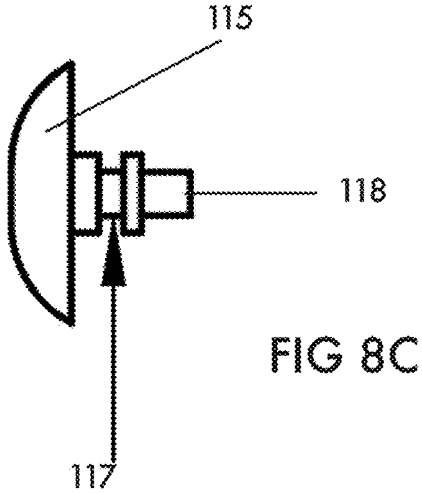
FIG 8C
FIG 8B
FIG 8D
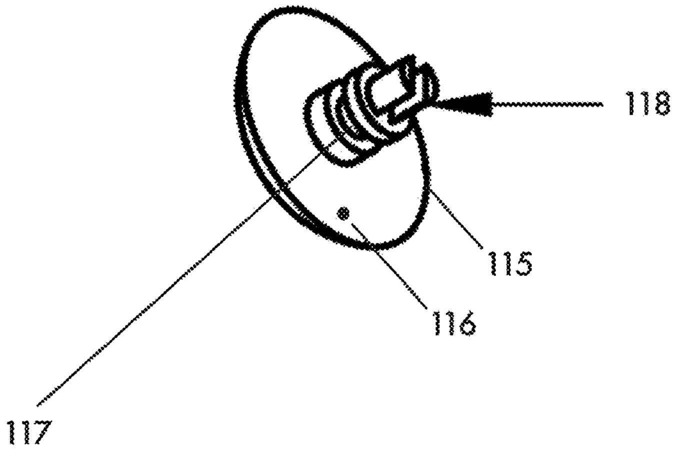

90 D °

45 D °

180 D °

FIG 10
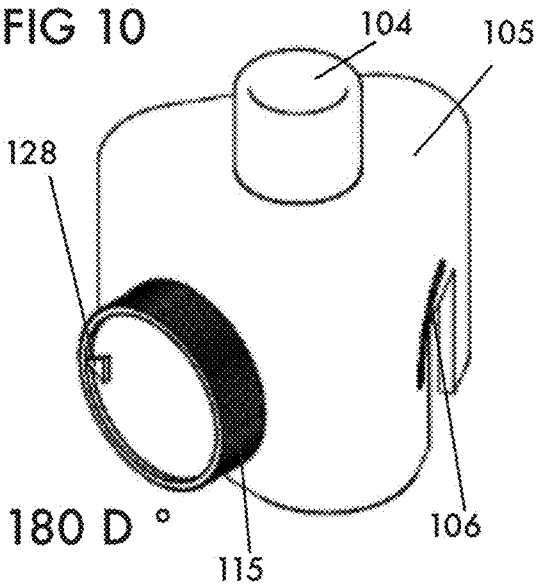
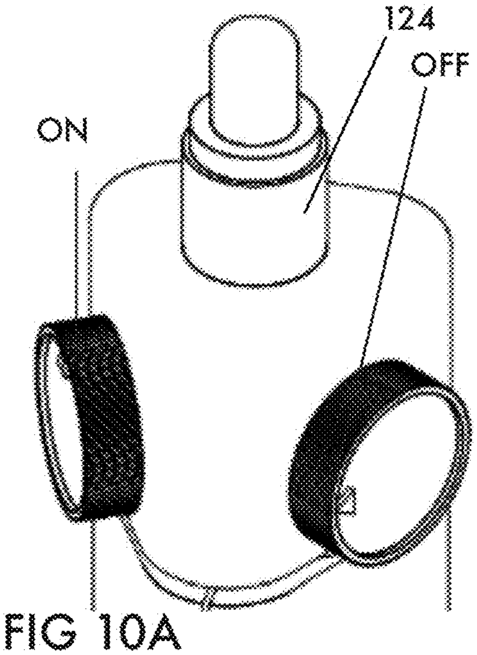
FIG 10A
FIG 10B
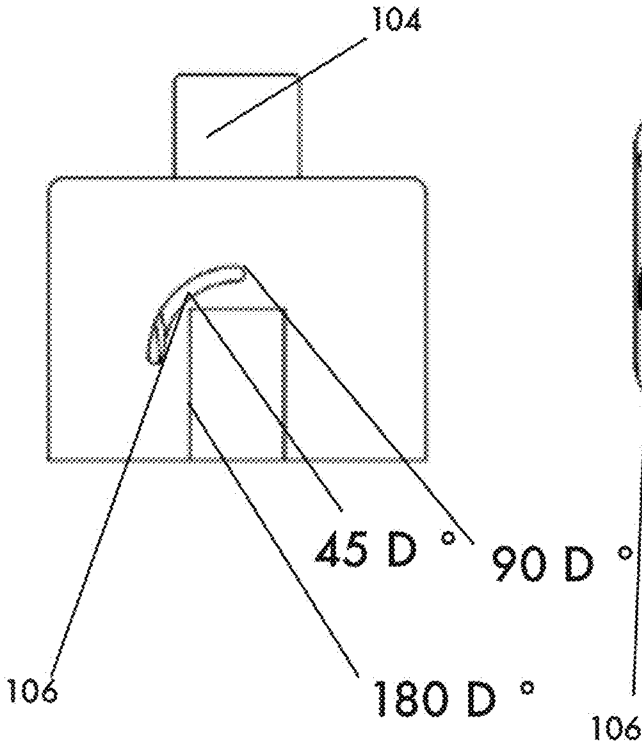
FIG 10C
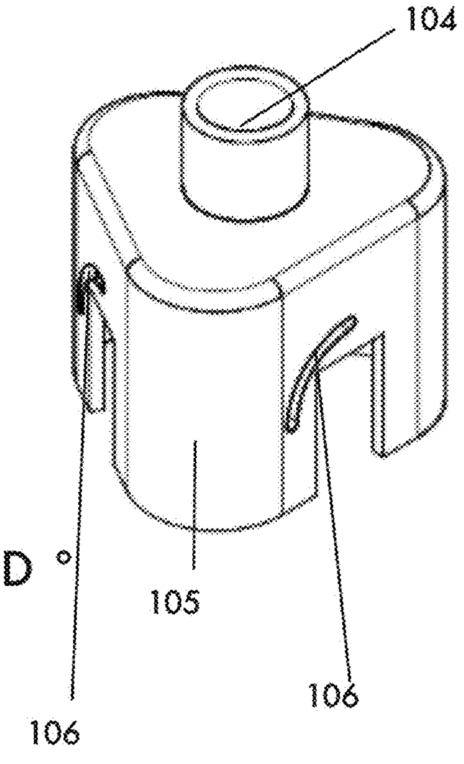

MULTI-COMPONENT VARIABLE CONTROL FRAGRANCE DISPENSING SYSTEM APPARATUS

PRIORITY

This application is a continuation-in-part of and claims the benefit of priority to U.S. patent application Ser. No. 17/366,693 entitled "MULTI-COMPONENT VARIABLE CONTROL FRAGRANCE DISPENSING SYSTEM APPARATUS" filed Jul. 2, 2021 which claims the benefit of priority to U.S. Provisional Patent Application No. 62/705,916 entitled "MULTI COMPONENT VARIABLE CONTROL FRAGRANCE DISPENSING SYSTEM APPARATUS" filed Jul. 22, 2020, the contents of which are incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of a fragrance or liquid dispenser. More particularly, the present disclosure relates to systems and methods for dispensing liquids and/or aerosols.

DESCRIPTION OF RELATED TECHNOLOGY

The fragrance consumer generally selects a fragrance based upon personal preference. A traditional fine fragrance has a scent selected by pre-combined solvents, oils, and/or other odoriferous materials into one container. The container is connected to an atomizer releasing such fragrance.

The combined solvents of a traditional fine fragrance are comprised of pre-measured compounds to ensure how the final product will be smelled by the consumer. A calculated chemical composition is generally what is called a signature fragrance to ensure consistency in smell.

A fragrance is typically broken down by (3) parts. The base, the middle, and top notes of the fragrance. Traditionally, the compounds have been selected by a perfumer, the compounds are combined into a single bottle with no room for customization or to change the compounds or smell as received by the customer. If the customer does not like just a single compound of the fragrance, there is no capability to change this.

SUMMARY

The present disclosure addresses the foregoing needs by disclosing, inter alia, methods, devices, and systems for variable control fragrance dispensing.

In one aspect, a system, methods, and apparatus configured to dispense fragrance (or other liquid) with variable control. One exemplary liquid dispensing apparatus includes: a plurality of containers, each container of the plurality of containers fillable with a different liquid of a plurality of liquids; a mixing chamber configured to receive and mix a variable amount of each of the plurality of liquids creating a mixed liquid; and a spray head configured to release the mixed liquid from the mixing chamber. In one variant, the liquid dispensing apparatus includes a plurality of valves associated with the plurality of containers and attached to the mixing chamber to control the variable amount of each of the plurality of liquids. This variant may include a plurality of selector knobs coupled to each of the plurality of valves, each of the plurality of selector knobs configured to control the plurality of valves and the variable amount of each of the plurality of liquids. In this variant, a first selector knob of the plurality of selector knobs is configured to, when rotated, adjust the variable amount of the different liquid of the plurality of liquids. In another variant, the mixing chamber is configured to receive the variable amount of each liquid at a same time causing the variable amount of each of the plurality of liquids to blend in the mixing chamber. In a further variant, the mixing chamber includes a plurality of passages connecting the plurality of containers. In another variant, at least one of the plurality of liquids includes a fragrance, a fragrance component, a solvent, and/or a skincare product.

In another aspect, a liquid dispensing apparatus is disclosed. One exemplary liquid dispensing apparatus includes a spray head with a pump; a first dip tube coupled to the spray head; a mixing chamber, coupled to the first dip tube; a plurality of valves coupled to the mixing chamber configured to control variable amounts of a plurality of liquids, each liquid of the plurality of liquids receivable from a different one of a plurality of attachable containers; a plurality of selector knobs coupled to and able to adjust the plurality of valves; a plurality of cap components coupled to the mixing chamber and each of the plurality of cap components attachable to the different one of the plurality of attachable containers; and a plurality of secondary dip tubes, each of the plurality of secondary dip tubes attach to the mixing chamber and pass through a cap component aperture in each of the plurality of cap components. In one variant, when the spray head is depressed, the pump forces liquid in the plurality of attachable containers up the plurality of secondary dip tubes and into the mixing chamber to create a blended liquid based a setting on each of the plurality of valves. In this variant, when the spray head is depressed, the blended liquid is forced through the first dip tube and out the spray head. In this variant, the pump includes a one-way valve to inhibit the blended liquid from flowing into the plurality of attachable containers. In another variant, the plurality of cap components are threaded to accept the plurality of attachable containers. In a further variant, the liquid dispensing apparatus includes a housing to cover the mixing chamber with openings for the plurality of selector knobs. In an even further variant, the liquid dispensing apparatus includes a housing including a plurality of guides to the plurality of selector knobs to meter the variable amounts of the plurality of liquids. In another variant, the first dip tube is coupled to the mixing chamber at a first mixing chamber aperture in the mixing chamber. In a further variant, the mixing chamber has a plurality of tubular passages radiating from a middle portion, the mixing chamber configured to receive the variable amounts of the plurality of liquids from the plurality of attachable containers where the variable amounts of the plurality of liquids blend in the middle portion of the mixing chamber.

In another aspect, an apparatus for mixing liquid is disclosed. One exemplary apparatus for mixing liquid includes a central portion includes a central cavity connected a first aperture; and a plurality of lateral arms extending from the central portion, wherein each of the plurality of lateral arms includes: a lateral arm cavity connecting to the central cavity; and a second aperture, the second aperture connectable to a second dip tube, the plurality of lateral arms each connectable to one of a plurality of valves configured to cover the second aperture a variable amount. In a variant, the apparatus for mixing liquid includes a rotatable selector knob coupled to a valve of the plurality of valves, the rotatable selector knob configured to control the valve when rotated. In another variant, the apparatus for mixing liquid includes the lateral arm cavity of each of the plurality of lateral arms includes a groove configured to hold an o-ring. In a further variant, the apparatus for mixing liquid includes a first dip tube coupled to the first aperture of the central portion and couplable to a pump and spray nozzle, wherein: each of the plurality of lateral arms is coupled to a plurality of secondary dip tubes, each of the plurality of lateral arms is couplable to a different one of a plurality of containers, and each of the plurality of secondary dip tubes configured to be inserted into the different one of the plurality of containers.

Other aspects, features and advantages of the present disclosure will immediately be recognized by persons of ordinary skill in the art with reference to the attached drawings and detailed description of exemplary embodiments as given below.

BRIEF DESCRIPTION OF THE DRAWINGS

FIG. 3 illustrates an exemplary perspective view of the device with certain parts assembled of the variable control selector knob in relationship to the entire fragrance dispensing device in accordance with various aspects of the present disclosure.

FIG. 3A through 3B illustrate an exemplary perspective view of the relationship of the mixing chamber to the sub-containers and variable control selector knob in accordance with various aspects of the present disclosure.

FIG. 8 illustrates an exemplary side sectional view of the mixing chamber attached to a variable control selector knob in accordance with various aspects of the present disclosure.

FIG. 8A illustrates an exemplary perspective view of the mixing chamber attached to a variable control selector knob and cap component in accordance with various aspects of the present disclosure.

FIG. 8B through 8D illustrate exemplary side and perspective views of a variable control selector knob in accordance with various aspects of the present disclosure.

FIG. 10 illustrates an exemplary perspective view of the variable control selector knob in the "off" position attached to the housing in accordance with various aspects of the present disclosure.

FIG. 10A illustrates an exemplary side view of the housing in relation to the variable control selector knobs in accordance with various aspects of the present disclosure.

FIG. 10B illustrates an exemplary perspective view of the variable control guides of the variable control selector knob to choose desired amounts of product concentrate in accordance with various aspects of the present disclosure.

FIG. 10C illustrates an exemplary isolated perspective view of the housing showing the plurality of the variable control guides to attach to the variable control selector knob in accordance with various aspects of the present disclosure.

DETAILED DESCRIPTION

Figure 1:
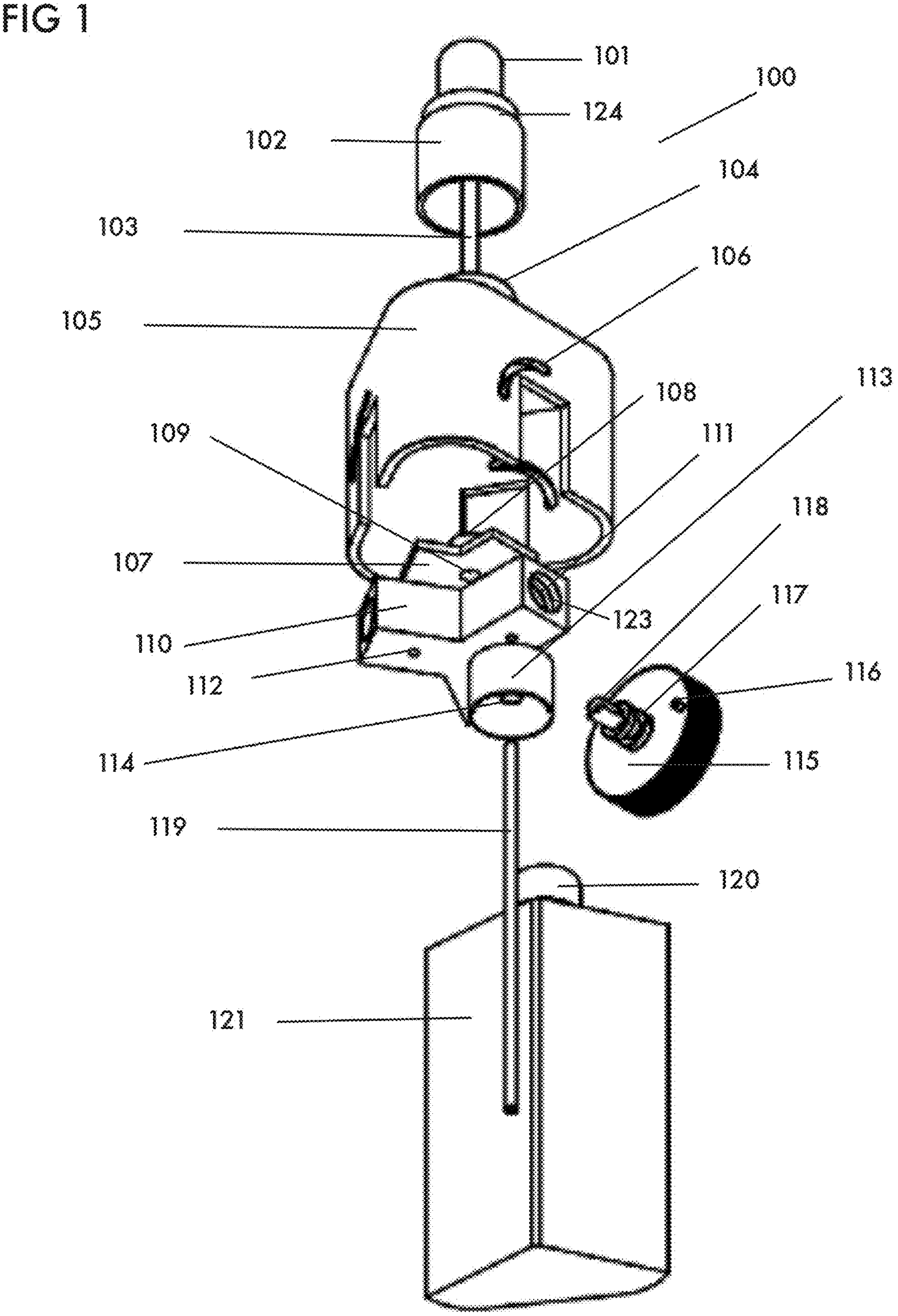
FIG. 1 illustrates an exemplary exploded view from below of the fragrance dispensing device in accordance with various aspects of the present disclosure.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding “one embodiment”, “an embodiment”, “an exemplary embodiment”, and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

Example Operation

The present disclosure gives a fragrance consumer the ability to choose what compounds in a fragrance they desire. In one embodiment, the apparatus has at least (2) or more separate sub-containers therein containing compounds separated from one another. Each sub-container can be interchanged for a different solvent compound yielding a different result to suit the taste of the consumer when the final spray from the apparatus is operated and controlled.

Embodiments of the disclosure relates generally to an apparatus for producing fragrance and more particularly to a fragrance dispensing device with removable sub-containers that can blend at least (2) liquid fragrance solvents into a single spray product. In addition, the device has variable control to select a percentage amount from 0%-100% of the maximum output per sub-container into the blended final product fragrance. There are practically an infinite number of combinations for the user to select. For example, a user selects A, X, and Y for sub-containers. The user selects 10% of A, 100% of Y and 30% of X. The next use the user switches amounts to 20% of A, 50% of Y, and 30% of X by turning respective knobs. The following day, X is switched out for sub-container C which is selected by the rotational knob to an output of 20%.

The method for applying fragrance has always been universally standard. A consumer buys the bottle of fragrance and the bottle emits one fragrance. The disclosed device brings customization to the fragrance industry. Interchanging sub-containers and selecting the amounts of each sub-container solve the problem of how fragrance is typically bottled in a fashion of pre-selected scents with no ability for an end user to customize.

While the present disclosure is described with the embodiment of a fragrance dispensing apparatus, this disclosure is not so limited. For example, in the beauty world there are other products formulated in a liquid form such as skin care. The present disclosure can also apply to the world of skin care where customization can be used to offer personalization for the unique needs of different skin.

Certain embodiments of the present disclosure include battery operated or use electrical wiring to aid in pumping. Other embodiments include a spray nozzle actuator operated by a motor and may be powered by a battery or other energy source.

Overall the device solves the problem for the average consumer buying fragrance. If one note of a fragrance is not desirable at a certain volume or at all, a user may switch out a sub-container in the device and start again. A fragrance can be as unique as the consumer holding it. Other features and advantages of the present disclosure will immediately be recognized by persons of ordinary skill in the art with reference to the attached drawings and detailed description of exemplary embodiments as given below.

Referring to the drawing, FIG. 1 is an illustrated exploded view of the fragrance dispensing device 100 with variable control. The exploded view can be seen fully assembled in FIGS. 2-2B. The fragrance dispensing device 100 has a top spray head actuator 101 that connects to a pump 124 within the housing component cover 102 by attaching to housing neck 104.

In one embodiment, spray head actuator 101 may include a spray nozzle to discharge liquid. The spray nozzle may include an atomizer to convert a stream of liquid into a mist or fine spray. The atomizer may break up the fragrance with a stream of air into small droplets and disburse the fragrance. The function of the spray head actuator is to dispense a mixed liquid. In another embodiment, spray head actuator may release non-atomized liquids and may include a lotion pump head to disburse thicker liquids such as lotions, creams, or soaps. In another embodiment, the device may include a syrup dispensing device for coffee drinks and the pump head includes a syrup pump-head.

In one embodiment, the fragrance dispensing device 100 has a top spray head actuator 101 that connects to a pump 124 within the housing component cover 102 by attaching to housing neck 104. Various embodiments may use a modular design that allows different parts to be swapped. Component swapping may be used for repair, to change functionality (e.g., different liquid to be dispensed), or alter aesthetic appeal. In an embodiment, the top spray actuator 101 and/or pump 124 may be swapped with another top spray actuator 101 and/or pump 124 by a user of the device. The change may be due to a change in the look of fragrance dispensing device 100, due to portions wearing out or breaking, or that offer different functionality. For example, a piston-based pump may be switched out for a compressible bulb pump for a particular fragrance application. A user may also replace or change the top spray actuator 101 and/or pump 124 to change between types of liquids, e.g., between fragrance to lotion to soap, or between desired amounts of final product to be dispensed from fragrance dispensing device 100. In one example, a fine mist of less than a milliliter of final product may be dispensed. In other examples, a dollop (an ounce or more) of final product may be dispensed into the hand of the user based on the use of the device. Each of the interchangeable top spray actuator 101 and/or pump 124 may attach to housing neck 104.

The main dip tube 103 is the supply line of the product concentrate to be retrieved from the mixing chamber 110.

The mixing chamber 110 is covered by a housing 105 that has multiple sides, and multiple variable control guides 106. The variable control guides 106 are located on the middle of the sides of housing 105 that encase the mixing chamber 110 and align with the variable control selector knobs 115. In one embodiment, variable control selector knobs 115 may be cylindrically shaped (as illustrated in FIG. 1), hemispherical (as illustrated in FIG. 8), rectangular, or a design with indentations for a user's fingers. In another embodiment, variable control selector knobs 115 may be a slider.

The variable control guides 106 meter the product concentrate to be released from each sub-container 121; in one exemplary implementation, the dispensed amount may be indicated by the knob's position and the control guide projection 116. In one embodiment, variable control guides 106 are a channel or cutout of housing 105 that control guide projection 116 fits in. When variable control selector knobs 115 are rotated, control guide projection 116 will move within the variable control guide 106. Control guide projection 116 may limit the movement of the variable control selector knobs 115 to a particular range of motion by having control guide projection 116 hit an edge of a variable control guide 106.

The variable control selector knobs 115 connect to the mixing chamber 110 on each lateral side to rotate left or right for controlling the amount of fragrance liquid product starting from 100%/on to 0%/off positions indicated by turning variable control selector knob 115. The amounts correlate to the dial indicator 128 angular direction on the variable control selector knob 115. Above the mixing chamber 110 is a secure adapter 107 with a top piece 108. Top piece 108 has an opening to allow the main dip tube 103 to pass from the housing component cover 102 through and retrieve the product concentrate from the mixing chamber 110 by a top opening 109 on the top side of the mixing chamber 110. The secure adapter 107 may hold main dip tube 103 in place and seal any mixed fragrance product released from top opening 109 of the mixing chamber 110 to the main dip tube 103 and not be released into the housing 105.

In the illustrated embodiment, mixing chamber 110 and the variable control selector knobs 115 are between top spray head actuator 101/pump 124 and sub-containers 121. In an alternative embodiment, top spray head actuator 101/pump 124 is between mixing chamber 110 and the variable control selector knobs 115 and sub-containers 121.

On the underside of the mixing chamber 110 is a plurality of mixing chamber openings 112 that connect to a cap component 113 and a sub-container dip tube 119 that feeds into sub-container 121 to retrieve the product concentrate. Sub-containers 121 may be fillable with different liquids. The cap component 113 fits on and attaches to the sub-container 121 at the sub-container neck 120 of sub-container 121. The sub-container dip tube 119 is connected to cap component 113 and/or a mixing chamber opening 112 of mixing chamber 110 and dips into sub-container 121. The sub-container 121 passes the product concentrate from each of the sub-containers 121 pre-selected by amounts from the variable control selector knobs 115. The product concentrate may then pass through the mixing chamber 110 by the plurality of mixing chamber openings 112 and through the passages 109A in the mixing chamber 110 up into the main dip tube 103. The now mixed final fragrance product may then pass to housing component cover 102 and finally sprayed through top spray head actuator 101.

In some embodiments, spray head actuator 101 and/or pump 124 may be interchangeable with other spray head actuators and/or pumps. For example, a user may select from a variety of different options for spray head actuator 101 and connect the selected spray head actuator 101 to the rest of the fragrance dispensing device 100 by a threading interface or may be snapped into place onto housing component cover 102.

In some embodiments, to ensure that final fragrance product is released through top spray head actuator 101, fragrance dispensing device 100 provides a sealed interior via, e.g., the secure adapter 107, O-ring groove 117 and an O-ring 123. Further components may be tightly connected components, or sealed using a glue/silicone/epoxy, or welded/fused together. This sealing may allow the transfer of pressure differences produced by pump 124 through fragrance dispensing device 100 to the sub-containers 121. Liquid product concentrate/mixing final product may then be transferred through mixing chamber 110 and out top spray head actuator 101.

In one embodiment, pump 124 contains a piston that is manually reciprocated. The piston may be mounted for reciprocating movement in the housing component cover 102, such that movement against a spring causes the piston to exert a compression force on the final product liquid in a pump liquid container inside pump 124. The compression force may cause the final product liquid through a passage in pump 124 to a nozzle of the spray head actuator 101. Release of the external downward force to the pump 124 permits the spring to expand under its restorative force, and to thereby return the pumping mechanism to its extended position. This movement of the pump mechanism causes the piston to move expanding the volume of the (sealed) mixing chamber 110 and sub-containers 121 in a manner which expands the interior volume. The negative pressure created by such movement draws liquid into the liquid chamber of pump 124. Valve assemblies may control the flow of final product liquid into the liquid chamber of pump 124 as the interior volume of liquid chamber of pump 124 is increased by the movement of the pump mechanism of pump 124.

In other embodiments, pump 124 includes a gas guide, a gas supply tube, and a compressible bulb (with two one-way valves) or a compressed gas tank to generate gas to spray. In one such embodiment, the compressible bulb stores air that when depressed moves quickly over main dip tube 103 pulling liquid in main dip tube 103 toward spray head actuator 101 (and liquid concentrate from sub-containers 121 into the mixing chamber 110). When the compressible bulb is depressed, a valve in the compressible bulb leading into the tube that leads toward spray head actuator 101 is forced open by air pressure and the valve leading to the outside environment is closed. When the compressible bulb is released, the compressible bulb returns to its original shape closing the valve leading to the tube towards spray head actuator 101 and opening the valve to the outside environment so that air can fill the compressible bulb.

In another embodiment, pump 124 is an electrically controlled pump that is controlled by a button press on fragrance dispensing device 100 or via a wireless interface.

In one embodiment, housing 105 comprises a processor coupled to a memory, a power source, and a network interface. An integrated circuit may include an electronic circuit manufactured by the patterned diffusion of trace elements into the surface of a thin substrate of semiconductor material. The processor may include an integrated circuit configured to execute instructions stored within memory. Memory includes any type of integrated circuit or other storage device configured to store digital data. The network interface includes an integrated circuit configured to communicate with another electronic device through wired or wireless means. The power source may include a battery or a wired or wireless power supply connectable to alternating or direct current.

In an exemplary embodiment, the network interface includes a wireless interface (e.g., Wi-Fi, personal area network (PAN) or Bluetooth interface). In this exemplary embodiment, pump 124 is an electronic pump that is wirelessly controllable by another device in communication via the network interface. The other device may include a phone device (e.g., a smart phone), a wearable (e.g., a smart watch), a computer (e.g., a desktop or laptop), or a remote control). In a further embodiment, flow control valves 118 are electronic valves that may be wirelessly controlled by the other device. The other device may send instructions to the fragrance dispensing device 100 to control whether and how much each of the flow valves 118 are open (or closed). The fragrance dispensing device 100 may receive the instructions via the network interface.

A product concentrate as used herein may include any liquid and can be made of several different compounds and product concentrates including but not limited to oils (including carrier oils), alcohols, naturally derived liquids, artificially created liquid chemical compounds, concentrated and natural liquids in a gel or cream base. Additionally, product concentrate may include syrups, alcohols, and other edible liquids. A product concentrate may also include commercially available or specially created eau de parfum or fine fragrance. Eau de parfum may be concentrated by a percentage of 11-20% of pure perfume or oil and the rest water and alcohol base. A fine fragrance mist or perfume may have a significantly higher ethanol or alcohol base (60%) and the rest be oil or chemically derived compounds. In one example, a product concentrate may include a single purified fragrance component or may include a non-fragrance component (e.g., a carrier oil or alcohol). Product concentrate may also include gel or cream components in, for example, skincare applications. Gels and creams may include any number of natural or synthetic oils, alcohols, fragrances, and/or medicinal compounds. The fragrance dispensing device 100 may combine, for example, an oil based serum, a cream moisturizer, and a gel like cream for personalized skincare.

Figure 2:
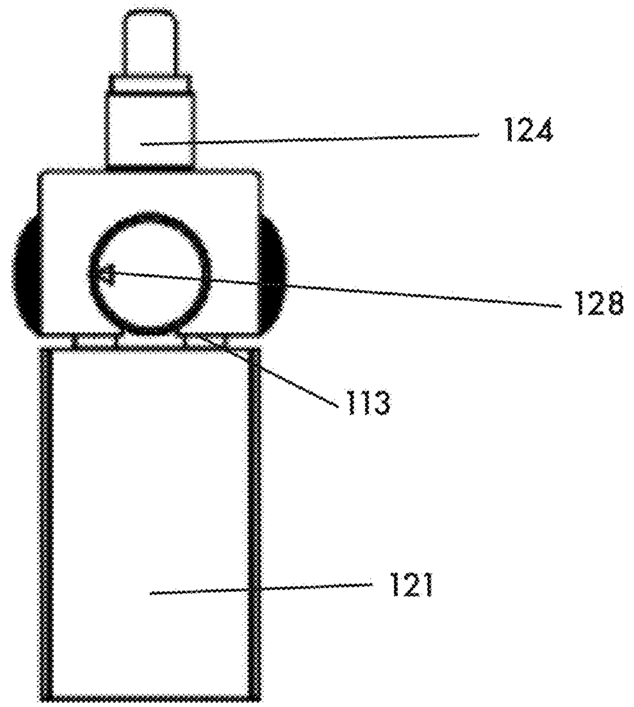
FIG. 2 illustrates an exemplary side view of the device and the components for control of each sub-container in accordance with various aspects of the present disclosure.

FIG. 2 is an illustrated side view of one side of the fragrance dispensing device 100. Each side may be identical by having a separate variable control selector knob 115, with a dial indicator 128, that connects to the mixing chamber 110 encased within the housing 105, and a sub-container 121. The dial indicator 128 on variable control selector knobs 115 can turn (with control selector knobs 115) clockwise or counter-clockwise or stop at any position in the middle to control the flow of product concentrate from each sub-container 121 to be released as a final spray product though top spray head actuator 101.

Figure 2A:
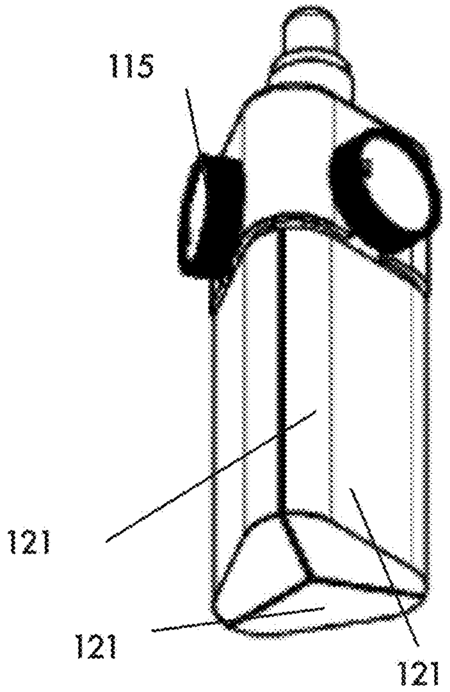
FIGS. 2A-2B illustrates an exemplary perspective view of the plurality of fragrance sub-containers and components bound together showing a completely assembled fragrance device in accordance with various aspects of the present disclosure.

FIG. 2A illustrates from a bottom perspective view of fragrance dispensing device 100 the plurality of the components of the device such as the variable control selector knob 115, the dial indicator 128, and the sub-containers 121.

Figure 2B:
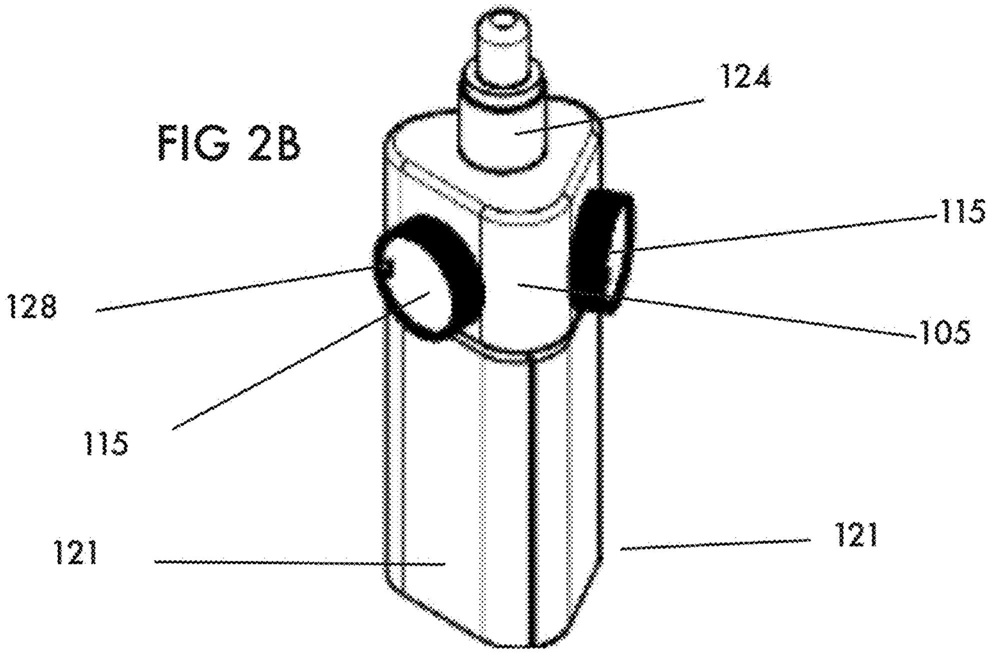

FIG. 2B illustrates a top perspective view of fragrance dispensing device 100 showing that all the variable control selector knobs 115 are attached and encased in the housing 105.

FIG. 3 illustrates a perspective view showing two sides of the fragrance dispensing device 100. The right side is shown fully assembled with a variable control selector knob 115 and a sub-container 121. On the left side, variable control selector knob 115 is removed to show the relationship of the variable control selector knob 115 attaching to the mixing chamber 110 by the lateral arm in. The variable control selector knob 115 is also attachable to the housing 105 and one of the variable control guides 106. The cap component 113 that attaches to the respective sub-container 121 can be seen under the housing 105 when the variable control selector knob 115 is removed.

FIG. 3A illustrates a perspective view from the side with the housing 105 removed. The mixing chamber 110 securely attaches to the variable control selector knob 115 by the lateral arm in of the mixing chamber 110. Under the mixing chamber 110 is the cap component 113 which holds one of the plurality of dip tubes 119 that retrieves product concentrate from one of the sub-containers 121.

FIG. 3B illustrates a perspective side view of fragrance dispensing device 100 with the housing 105 removed. The secure adapter 107 is removed to show the top opening 109 on top of the mixing chamber 110 in which the liquid fragrance product blend flows from the passages 109A (as illustrated in FIG. 5A) inside the mixing chamber 110.

Figure 4:
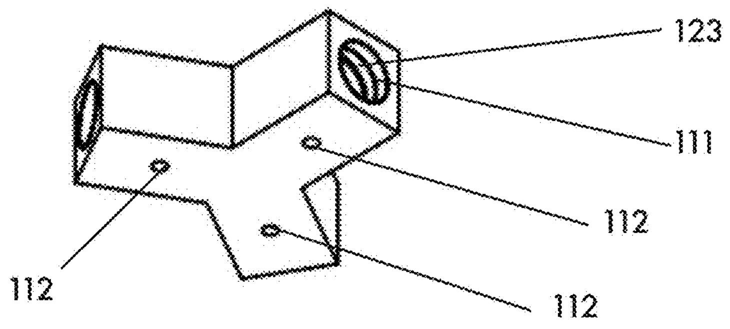
FIG. 4 illustrates an exemplary perspective view from below of the mixing chamber in accordance with various aspects of the present disclosure.

FIG. 4 illustrates a perspective view from below of the mixing chamber 110. The bottom portion can include 2 or more mixing chamber openings 112 that feed the product concentrate to the passages 109A of mixing chamber 110. The number of mixing chamber openings 112 match the number of sub-containers 121 per fragrance dispensing device 100. The mixing chamber openings 112 of the mixing chamber 110 retrieve the product concentrate from the sub-container 121 supplied by the sub-container dip tube 119 and connected by the cap component 113. The lateral arm in of the mixing chamber no is shown which connects to the variable control selector knobs 115 engaging the flow control valve 118 on the variable control selector knob 115. Inside the lateral arm 111 within the mixing chamber 110 is an O-ring groove 117 that holds an O-ring 123 that prevents fragrance liquid product concentrate from leaking out variable control selector knob 115.

In the illustrated embodiment, three-equally-spaced lateral arms 111 come out of mixing chamber 110. In alternative embodiments, a greater or fewer number of lateral arms in may be used (e.g., two, four, etc.) and the arms may be equally spaced or variably spaced. In a variably-spaced embodiment, sub-containers 121 of different volumes may be used with different kinds of liquids (carrier oil/alcohol/base and fragrance concentrates) or based on a user preference (the user may install and use a larger (or smaller) sub-container of a particular preferred fragrance component).

Figure 4A:
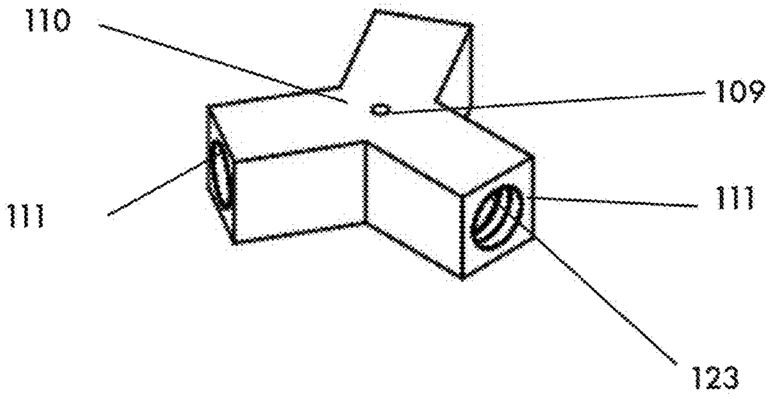
FIG. 4A illustrates an exemplary perspective view from above of the mixing chamber in accordance with various aspects of the present disclosure.

FIG. 4A illustrates a perspective view of the top side of the mixing chamber no. Top opening 109 retrieves product from inside the passages 109A of mixing chamber no. The top opening 109 supplies the product concentrate to the main dip tube 103 for the housing component cover 102 for a final fragrance product from the top spray head actuator 101.

Figure 5:
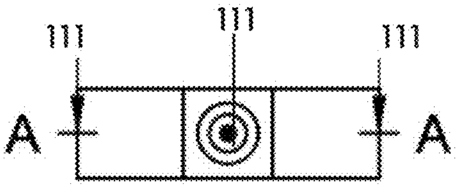
FIG. 5 illustrates an exemplary side sectional view of the mixing chamber in accordance with various aspects of the present disclosure.
Figure 5A:
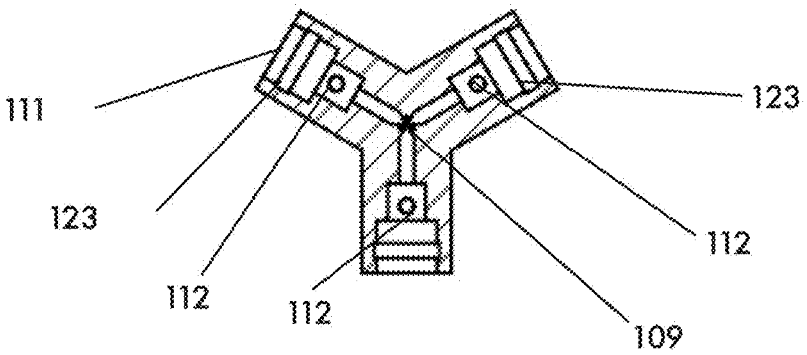
FIG. 5A and FIG. 5B illustrate an exemplary cross sectional view of the mixing chamber and a cross sectional view of each lateral side in accordance with various aspects of the present disclosure.

FIG. 5 illustrates a side cross-sectional view of the mixing chamber 110 and the plurality of the lateral arms in that hold the variable control selector knobs 115 to attach to the variable control selector knobs 115 to a respective flow control valve 118 of the fragrance dispensing device 100.

FIG. 5A illustrates a cut away cross-sectional view from below of the mixing chamber 110 to show the passages 109A. Passages 109A may receive the product concentrate fed by the respective mixing chamber openings 112 that connect to the sub-containers 121. The product concentrate from each of the sub-containers 121 flows through the plurality of mixing chamber openings 112. As shown in FIG. 3A, the product concentrate is retrieved from the sub-container dip tube 119 in their respective sub-containers

121, through the cap component 113, up into the mixing chamber opening 112, and into the mixing chamber 110 by the passages 109A in the mixing chamber 110. The selected amount of product concentrate per sub-container 121 is achieved by moving the variable control selector knob 115 attached to the lateral arm in. The liquid amount regulated to flow by the flow control valve 118 is forced by depression of the top spray head actuator 101. The liquid is retrieved from each sub-container 121 by the action of the user depressing the top spray head actuator 101. The specific selected amount of product concentrate in each final spray is chosen, as indicated by the position of dial indicator 128, based on the position of variable control selector knob 115 (as shown in FIGS. 9B-9D), which then flows through the passages 109A of the mixing chamber 110. Product concentrates blend together in the mixing chamber 110 and meet at top opening 109 for a final product to be released by the mixing chamber 110 via the top opening of 109. Once out of the top opening of 109, the mixed final product is retrieved by the main dip tube 103 that reaches the top spray head actuator 101 when depressed into the component of the housing component cover 102 for a final fragrance product.

Figure 5B:
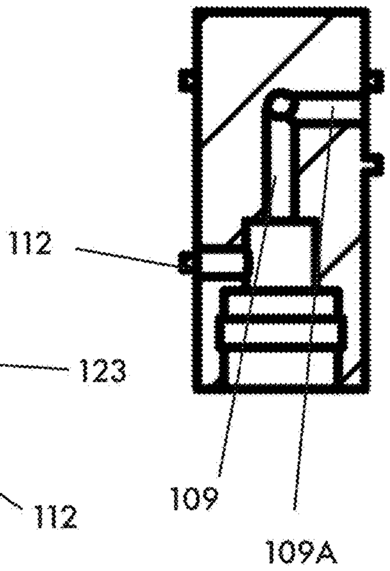

FIG. 5B illustrates a cross-section of each lateral arm 111 of the mixing chamber 110. The mixing chamber openings 112 are connected to the respective passages 109A that flow into the center of mixing chamber 110 through top opening 109. The O-ring groove 117 holds the O-ring 123 to keep the product concentrate from leaking out lateral arm in.

Figure 6:
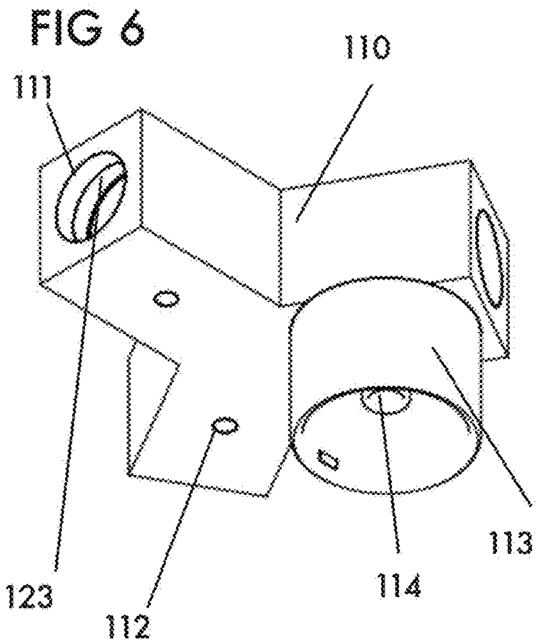
FIG. 6 illustrates an exemplary perspective view from below of the mixing chamber attached to a cap component in accordance with various aspects of the present disclosure.
Figure 6A:
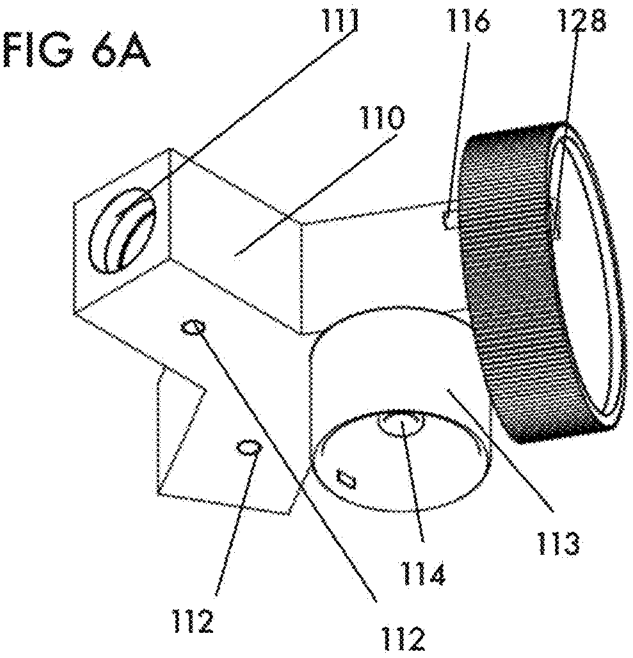
FIG. 6A illustrates an exemplary perspective view from below of the mixing chamber in accordance with various aspects of the present disclosure.
Figure 6B:
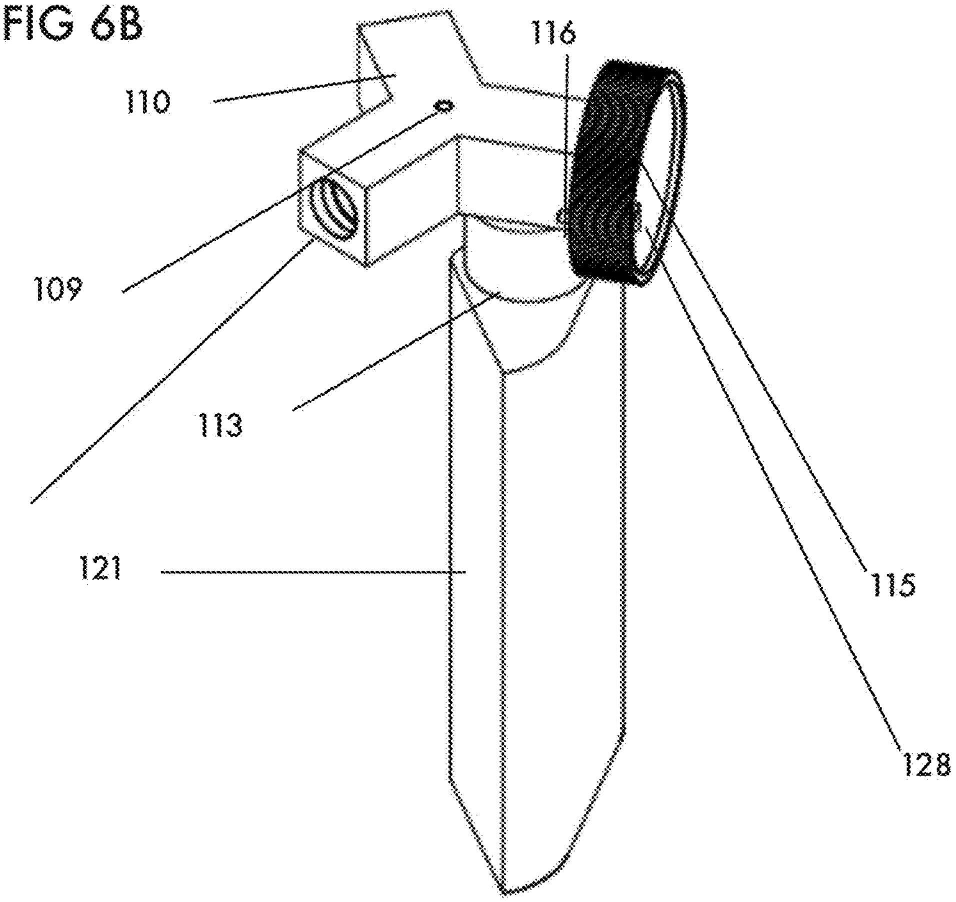
FIG. 6B illustrates an exemplary perspective view from below of the mixing chamber as assembled with one attached sub-container in accordance with various aspects of the present disclosure.

FIG. 6 illustrates a bottom perspective view of the mixing chamber 110 to show the relationship of the cap component 113 to the mixing chamber openings 112 and the sub-container 121 shown in referring to FIG. 6B. Cap component 113 includes a middle opening 114 that holds the sub-container dip tube 119 that flows the product concentrate from sub-container 121.

FIG. 6A illustrates a bottom perspective view of the mixing chamber 110 attached to one of the variable control selector knobs 115. Each of the variable control selector knobs 115 is attached to the mixing chamber 110 and the flow control valve 118 on the other side of the variable control selector knob 115 is inserted into the mixing chamber 110. The variable control selector knob 115 controls the respective sub-container 121 indicated by the cap component 113 when attached.

FIG. 6B illustrates a partially assembled perspective view from above of the fragrance dispensing device 100 with the mixing chamber 110 attached to a variable control selector knob 115 in relation to a sub-container 121 and cap component 113 assembled on one side. The sub-container dip tubes 119 in the sub-container 121 when assembled are hidden (as shown in FIG. 3B) and can be engaged with the rest of the fragrance dispensing device 100 to retrieve a liquid fragrance product inside the sub-container 121.

Figure 7:
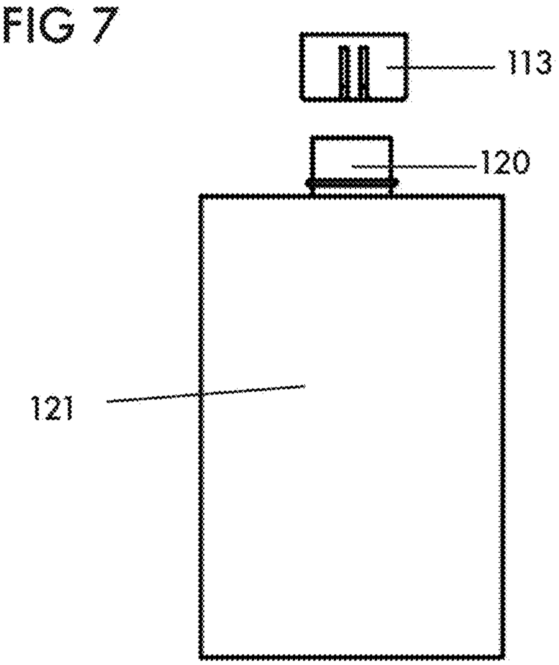
FIG. 7 illustrates an exemplary isolated side view of the sub-container detached from the cap component in accordance with various aspects of the present disclosure.

FIG. 7 illustrates a side view of the sub-container 121 isolated to show the relationship and attachment to the cap component 113. The cap component 113 holds the connecting sub-container dip tube 119 by middle opening 114 of the cap component 113 that holds the sub-component dip tube 119 to retrieve the product concentrate inside of the sub-container 121. The cap component 113 may be attached by the sub-container neck 120 of the sub-container 121 and may fit the cap component 113 securely such that liquid cannot escape. This design of the cap component 113 and sub-container 121 may be varied depending on the shape of fragrance dispensing device 100. The sub-container dip tube 119 is firmly secured to the cap component 113 through the middle opening 114 in the center on the underside of the cap component 113 as shown in more detail in FIG. 7B and FIG. 7C.

Figure 7A:
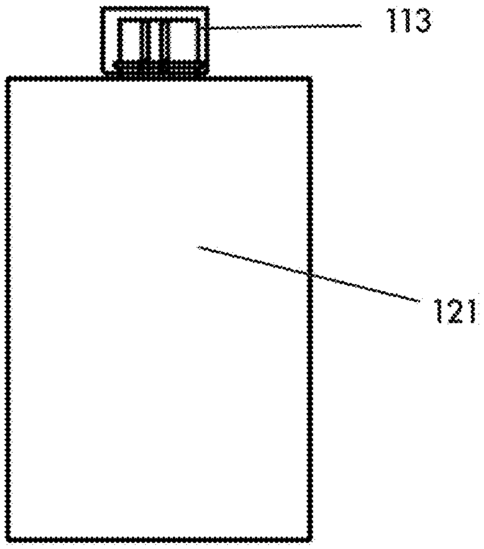
FIG. 7A illustrates an exemplary isolated side view of the sub-container attached to the cap component in accordance with various aspects of the present disclosure.

FIG. 7A illustrates the sub-container 121 with the cap component 113 attached. The cap component 113 can be manufactured with or without the middle opening 114. With no middle opening 114 on the cap component 113 the user may securely hold the product concentrate from spilling when not attached to the fragrance dispensing device 100. Cap component 113 attaches securely to the neck of the sub-container 121.

The sub-container 121 can be removed from the fragrance dispensing device 100 (as shown in the exploded view of FIG. 1) or included (as shown in to FIG. 2) to change out the product concentrates in sub-container 121 to be blended for a final product from the top spray head actuator 101. Fragrance dispensing device 100 may be constructed using resin, glass, plastic, polyurethane, and crystal. Each sub-container 121 can be removed and stored with a cap component 113 that does not include a middle opening 114 for retrieving product. Each time the sub-container 121 filled with a different type of product concentrates is changed, the final product combination blended in the mixing chamber 110 with product concentrates from other sub-containers 121 changes (when the respective variable control selector knob 115 is not set to an "off" position).

Figure 7B:
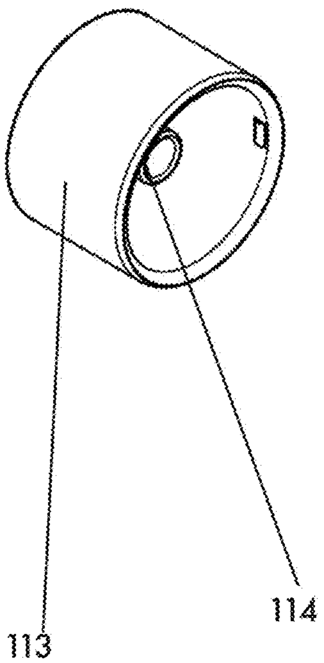
FIG. 7B-7C illustrates an exemplary isolated perspective and side view of the cap component in detail in accordance with various aspects of the present disclosure.

FIG. 7B illustrates a side view of the cap and the middle opening 114 in relation to the underside of the cap component 113.

Figure 7C:
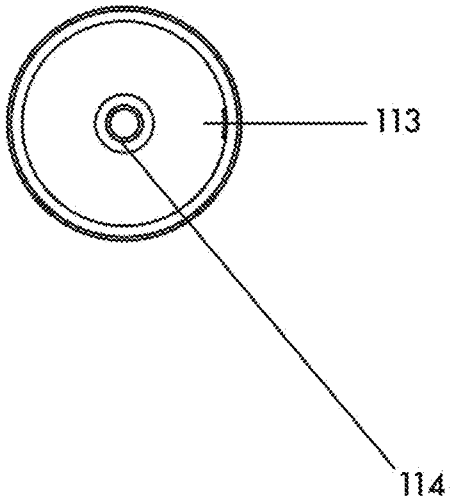

FIG. 7C illustrates a side view of the bottom of the cap component 113 and the middle opening 114 for product retrieval that is placed directly in the center of cap component 113.

FIG. 8 illustrates a side view of the mixing chamber 110 and the plurality of the lateral arms in and mixing chamber openings 112 on the bottom of mixing chamber 110 that connect to the sub-containers 121.

FIG. 8A is a top perspective view of the mixing chamber 110 and the connection to the sub-container 121. The sub-container 121 is attached to the mixing chamber opening 112 by the secure attachment of the cap component 113. When the variable control selector knob 115 is attached to the mixing chamber 110 by the lateral arm in the sub-container 121 components easily fit underneath and the cap component 113 attaches to the mixing chamber openings 112 112 on the bottom of the mixing chamber no seen in reference to FIG. 6A. Not shown is the sub-container dip tube 119 that attaches to the middle opening 114 of the cap component 113. Product concentrate is forced up the sub-container dip tube 119 from the sub-container 121 when top spray head actuator 101 is pressed forcing air (or another gas/liquid) to be pumped into sub-container 121.

FIG. 8B illustrates a back side view of the flow control valve 118. Referring also to FIG. 10B, the variable control selector knobs 115 can be rotated clockwise or counterclockwise guided by the control guide projection 116 when the flow control valve 118 is inserted into the lateral arm in of the mixing chamber 110 (as illustrated in referring to FIG. 3).

Flow control valve 118 adjusts the amount of product concentrate that is able to flow into the mixing chamber 110. Control guide projection 116, when fit inside of variable control guide 106, limits the amount of movement of flow control valve 118 to a particular set of angles. In one position of flow control valve 118, the liquid is full on (100%) (as shown in FIG. 9B). In another position, the liquid is full off (0%) (as shown in FIG. 9D). All positions in between can be used to block liquid flow (e.g., 50%) (e.g., as shown in FIG. 9C).

In the illustrated position, in FIG. 8B, of the flow control valve 118, the control guide projection 116 is parallel to the half circles of the flow control valve 118 indicating "on" or 100%. This adjusts the amount of liquid concentrate that may flow into the mixing chamber 110. In between the circles is a vertical passage that allows liquid to flow up in from the mixing chamber opening 112 on the mixing chamber 110. There is no blocking the mixing chamber openings 112 or the passages 109A of mixing chamber 110 in this position (as shown in FIG. 5A). The half circles of the flow control valve 118 are not blocking the two openings of mixing chamber openings 112 and passages 109A into the mixing chamber 110. When the semi-circular valve components of the flow control valve 118 are turned and are in a horizontal position the dial is also now horizontal indicating "off" or 0%. The semi-circular valve components are now blocking the opening of mixing chamber opening 112 and passages 109A and no liquid can flow. If the semi-circular valve components of flow control valve 118 are rotated to the vertical position by rotating the knob 115 50% of the way or direction, only 50% of the maximum amount of product concentrate can flow when the top spray head actuator 101 is pressed because mixing chamber opening 112 is blocked halfway.

FIG. 8C illustrates a side view of the variable control selector knob 115 and flow control valve 118. The flow control valve 118 can be shown to have an O-ring groove 117 (to be filled with O-ring 123) that keeps the product concentrate from leaking from the mixing chamber 110.

FIG. 8D illustrates a perspective view of the variable control selector knob 115 and flow control valve 118. The flow control valve 118 allows product concentrate to flow through the flow control valve 118 in this position from the mixing chamber opening 112. The O-ring groove 117 can accommodate an O-ring 123 for protection from leaking.

Figure 9:
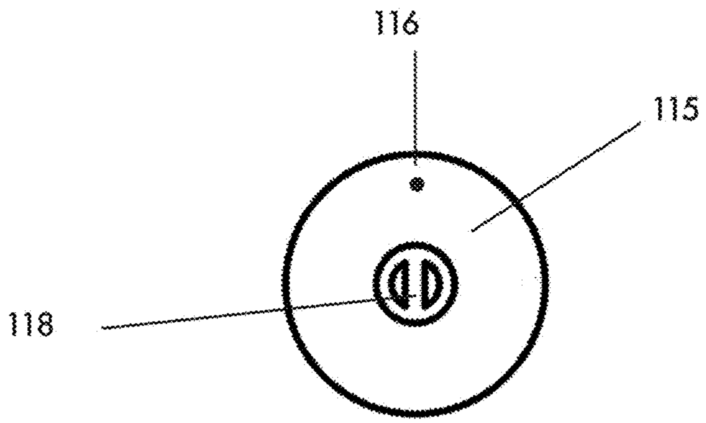
FIGS. 9 and 9A illustrate an exemplary side and cross-sectional view of the variable control selector knob in accordance with various aspects of the present disclosure.

FIG. 9 illustrates the flow control valve 118 in the "off" position with the circles horizontal. This blocks the mixing chamber openings 112 and passages 109A of mixing chamber 110. The product concentrate can flow into the sub-container dip tube 119 but will not reach the mixing chamber 110 and flow back into its respective sub-container 121.

Figure 9A:
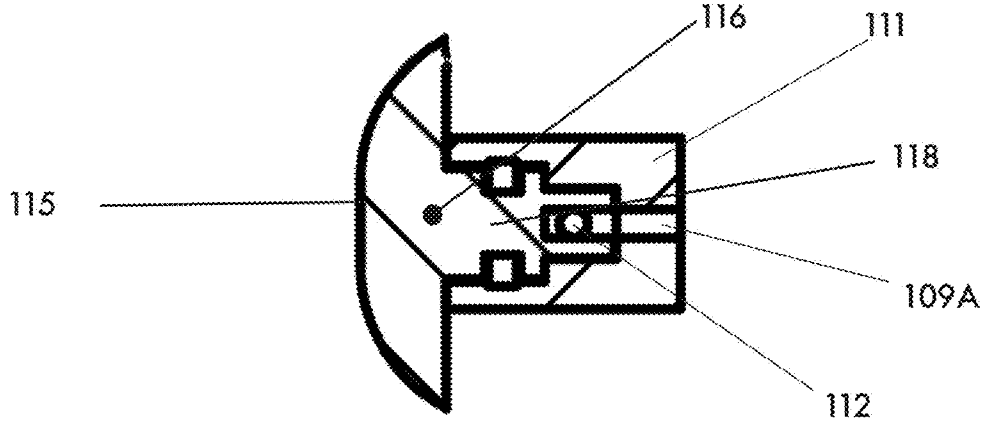
Figure 9B:
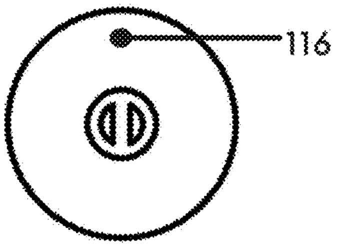
FIG. 9B through 9D illustrates an exemplary side view of the variable control selector knob in different angular positions in accordance with various aspects of the present disclosure.
Figure 9C:
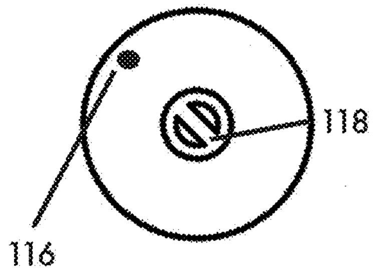
Figure 9D:
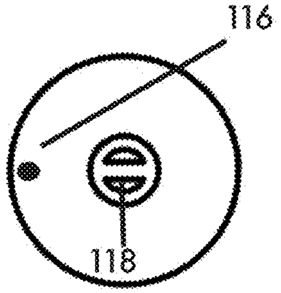

FIG. 9A is a cross-section view of the variable control selector knob 115 inserted into the lateral arm in of the mixing chamber 110. The cut away shows the control guide projection 116 in a position to the top, 90 degrees, or "on." The passages in semi-circular valve components of the flow control valve 118 are vertical and product concentrate can pass through to the mixing chamber opening 112 that is not closed/covered that supplies the product concentrate to the passages 109A of mixing chamber 110. Any position of the semi-circular valve components of the flow control valve 118 in-between completely horizontal or vertical is a qualitative percentage amount of liquid concentrate to flow from the mixing chamber opening 112. For example, if the variable control selector knob 115 is turned one third of the way from on to off, the circular valve components of the flow control valve 118 allow approximately one third of the product concentrate to flow through the flow control valve 118 and into the passages 109A of mixing chamber 110.

FIGS. 9B-9D illustrates the variable control selector knob 115 and flow control valve 118 in various degree positions that either block or allow the amount of liquid indicated on the control guide projection 116 to be received into the mixing chamber 110.

FIG. 9B illustrates a side view of the back of the flow control valve 118 in an "on" position by control guide projection 116 (or the dial indicator 128 on the reverse side of variable control selector knob 115) in a go-degree position. The flow control valve 118 has both circular valve components in a vertical position not blocking the mixing chamber opening 112 or when inserted into lateral arm 111 attached to passages 109A of mixing chamber 110 not at all or 0%. The product concentrate from 121 can flow at 100% when the top spray head actuator 101 is depressed and liquid is forced to spray from the top spray head actuator 101.

FIG. 9C illustrates a side view of the back of the flow control valve 118 with the by control guide projection 116 (or the dial indicator 128 on the reverse side of variable control selector knob 115) at a 45-degree angle allowing for 50% of the product concentrate to be retrieved from the sub-container 121 and to be released into the passages 109A of mixing chamber 110. The flow control valve 118 is rotated in a 45-degree angle where one of the half circles of the circular valve components of flow control valve 118 are blocking half or 50% of the mixing chamber opening 112 and half of the opening of passage 109A into the mixing chamber 110.

FIG. 9D illustrates a side view of the back of the flow control valve 118 with the by control guide projection 116 (or the dial indicator 128 on the reverse side of variable control selector knob 115) at a 180-degree angle and the flow control valve 118 in a horizontal "off" position for 0% of the product concentrate to flow through the mixing chamber opening 112 or enter the passages 109A of the mixing chamber 110 fed from the sub-containers 121.

FIG. 10 illustrates a perspective view of the housing 105 with one variable control selector knob 115 attached showing the relationship of the dial indicator 128 (and/or the control guide projection 116) to the variable control guide 106. When the variable control selector knob 115 is turned with the dial indicator 128 (and/or the control guide projection 116) to the far left or 180-degree "off" position the product concentrate cannot be retrieved and little or no product concentrate will be released into the mixing chamber 110 from sub-container dip tube 119.

FIG. 10A illustrates a perspective view of the housing 105 with a plurality of variable control selector knobs 115 attached. The right variable control selector knob 115 is "off" shown by the dial indicator 128 (and/or the control guide projection 116) in a left counterclockwise position or 180-degree angle. The left variable control selector knob 115 is "on" shown by the go-degree of the dial indicator 128 (and/or the control guide projection 116) up or "on".

FIG. 10B illustrates a side view of the housing 105 and the relationship of the variable control guide 106 for variable control selector knobs 115 and the control guide projection 116 (and/or the dial indicator 128) correlating to the amount of the liquid product to be released. When a variable control selector knob 115 and control guide projection 116 (and/or the dial indicator 128) is in a 180-degree angle, 0% of the product concentrate will be released by force from the top spray head actuator 101. When the variable control selector knob 115 and control guide projection 116 (and/or the dial indicator 128) is in a 45-degree angle, 50% of the product concentrate will be released by force from the top spray head actuator 101 attached to the mixing chamber 110 for a final fragrance product combined with the product concentrates contained in other sub-containers 121. When the variable control selector knob 115 and control guide projection 116 (and/or the dial indicator 128) is in a go-degree angle, 100% of the product concentrate will be released by pressure from the top spray head actuator 101 attached to the housing neck 104 for a final fragrance product combined with other sub-containers 121 product concentrates retrieved from top opening 109 of mixing chamber 110.

FIG. 10C illustrates a side-isolated perspective view of the housing 105 to show the plurality of variable control guides 106 and the attachment to the top spray head actuator 101 and housing component cover 102.

Figure 11:
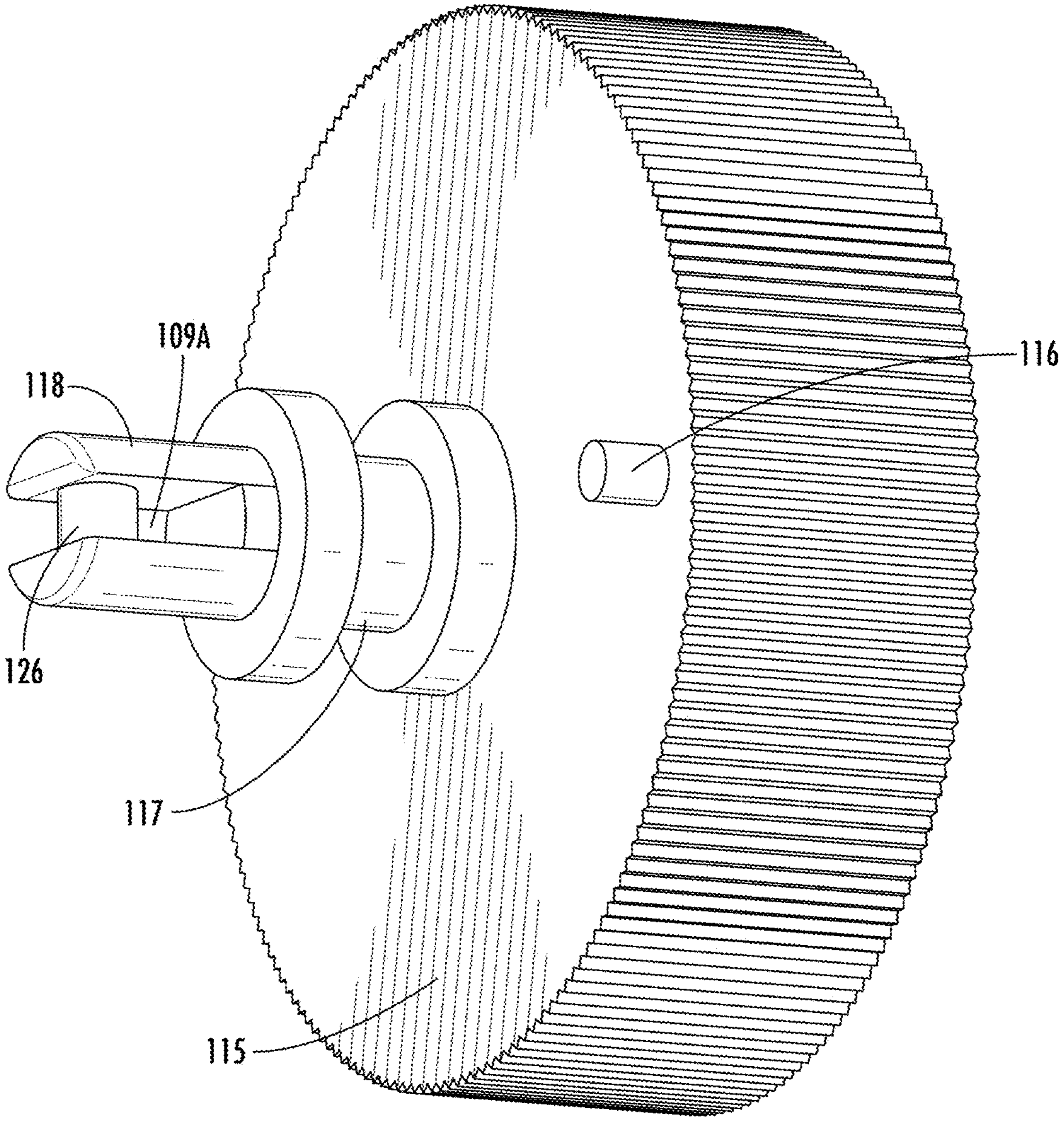
FIG. 11 illustrates an exemplary side view of the variable control selector knob in accordance with various aspects of the present disclosure.

FIG. 11 illustrates a side view of the variable control selector knob 115. Variable control selector knob includes the control guide projection 116, and is attached to flow control valve 118. Flow control valve 118 includes an O-ring groove 117 that can be fitted with O-ring 123 in order to stop liquid from leaking out from the variable control selector knob 115 during use, when flow control valve 118 is set inside lateral arm 111 of mixing chamber 110. Flow control valve 118 is depicted as having two arms. Brace 126 is used to stabilize the two arms of control valve 118 so it may effectively block all or a certain percentage (from 0 to 100%) of liquid concentrate/liquid fragrance product from traveling through mixing chamber openings 112 into the mixing chamber 110.

Variable control selector knob 115 may include outer ridges to aid gripping by a user. The outer ridges may be substituted by someone of ordinary skill with equal success with, for example, other textures. In a variant, variable control selector knob 115 is covered with material with a high co-efficient of friction with skin or common fabrics/leather used in gloves such as silicone.

In other embodiments, variable control selector knob 115 may include a knob, an elongated handle, latch, a winged knob or any other type of handle that can control flow control valve 118.

Control guide projection 116 may be used to limit the movement of variable control selector knob 115 when the variable control selector knob 115 is connected to housing 105. The variable control guides 106 on housing 105 physically limits the movement of the variable control selector knob 115 to a certain range of rotating angles (e.g., a quarter turn or 90°) by providing a physical barrier that control guide projection 116 will catch or collide with. This stops the movement of variable control selector knob 115. In the illustrated embodiment, the variable control guides 106 represent a cutout portion for the dial indicator to sit inside. In other embodiments, variable control guides 106 may be extensions from housing 105 that impede the movement of the variable control selector knob 115. The range of angles correspond to different settings of the variable control selector knob 115 and of control valve 118.

Flow control valve 118 physically impedes or facilitates the flow of liquid concentrate from a sub-container 121 (through the associated dip tube 119) by blocking or unblocking (either partially or fully) a mixing chamber opening 112. As shown, flow control valve 118 is a butterfly or quarter turn valve. The arms of flow control valve 118 turn when the variable control selector knob 115 is rotated. When the arms of flow control valve 118 rotate and cover/exert pressure on mixing chamber opening 112, mixing chamber opening 112 is sealed not allowing liquid concentrate to be pulled into the mixing chamber 110 from the sub-containers 121.

Flow control valve 118 may include brace 126 to stabilize the arms of flow control valve 118. Brace 126 may provide structure to the arms of flow control valve 118 so the arms do not bow inward, towards each other, and fail to produce a seal over mixing chamber opening 112. In some embodiments, brace 126 may extend such that the arms of flow control valve 118 bow slightly outward, away from each other, to insure a seal that presses into the mixing chamber opening 112 when flow control valve 118 is closed (or "off"). This configuration for arms of the flow control valve 118 may be used, for example, in embodiments where the flow control valve 118 or mixing chamber 110 is made out of a material that deforms or compresses under pressure such that a liquid seal would not occur between the flow control valve 118 and mixing chamber opening 112 of mixing chamber 110. Brace 126 may be used when flow control valve 118 and/or mixing chamber no is made of particular materials. For example, less rigid materials, e.g. plastics, may compress or deform more than others, e.g., metals, and brace 126 may provide additional support in those embodiments.

In another embodiment, flow control valve 118 may also include a ball valve where a ball with a hole is controlled by variable control selector knob 115, and when the hole is over mixing chamber opening 112, liquid concentrate is allowed to pass into the mixing chamber 110. When another portion of the ball is covering mixing chamber opening 112, liquid concentrate is allowed to pass into the mixing chamber 110. When flow control valve is partially opened and partially closed, in the middle of the "on" and "off" positions, and where the hole in the ball is partially covered, liquid concentrate may pass to a varying degree based on how much coverage of the mixing chamber opening is open.

In other embodiments, flow control valve 118 may include one or more of a gate valve, a globe valve, a straight or angled stop valve, a check valve, a plug valve, or a diaphragm valve.

Passages 109A in mixing chamber 110 may extend through the flow control valve 118. When the flow control valve 118 is opened (or "on"), passages 109A extend to meet mixing chamber openings 112. When the flow control valve 118 is closed (or "off"), passages 109A extend up to the valve and do not meet mixing chamber openings 112.

O-ring groove 117 may be fit with O-ring 123. O-ring 123 may sit within 0-ring groove 117 and create a seal between flow control valve 118 and the lateral arms in of mixing chamber 110. A proper seal insures liquid concentrate and blended final product do not leak out the lateral arms 111 and through the flow control valve 118. A seal also allows for the liquid concentrate to be mixed and directed out top opening 109 of mixing chamber 110.

Side Valve Design

According to aspects of the present disclosure, a fragrance dispensing device features a valve with valve controls that rotate clockwise and counterclockwise partially within a housing. The variable control selector knobs 115 (of FIG. 1) are disposed external to the housing 105 in an upright orientation situated on the sides of the mixing chamber, the valve may be open and closed with a lateral rotation of the valve controls of the fragrance dispensing device (when the fragrance dispensing device is held upright with the sub-containers at the bottom and the top spray head actuator at the top of the fragrance dispensing device).

While described with respect to dispensing fragrances/perfumes, as would be appreciated by those of ordinary skill, the described techniques may be applied to other fluids (as described elsewhere herein). For example, more viscous fluids (e.g., lotions, creams, edible liquids) may be mixed and applied using the foregoing techniques. Additionally, mixed fluid types may be mixed using the foregoing techniques. For example, a non-fragranced base lotion or carrier oil may be contained in one sub-container and fragrances in other sub-containers. In such an example, the sub-containers may be of differing sizes. For example, a larger sub-container for the base lotion/oil and smaller sub-containers for the fragrances). The amount of the base lotion/oil and fragrances may differ varying the dip tube/mixing chamber tube sizing, additional pump components, etc. as a properly mixed final product may have a greater quantity of base lotion/oil to fragrance concentrates. Additionally, the user (using the valve controls) may alter the relative quantities that are dispensed from the sub-containers.

Figure 12:
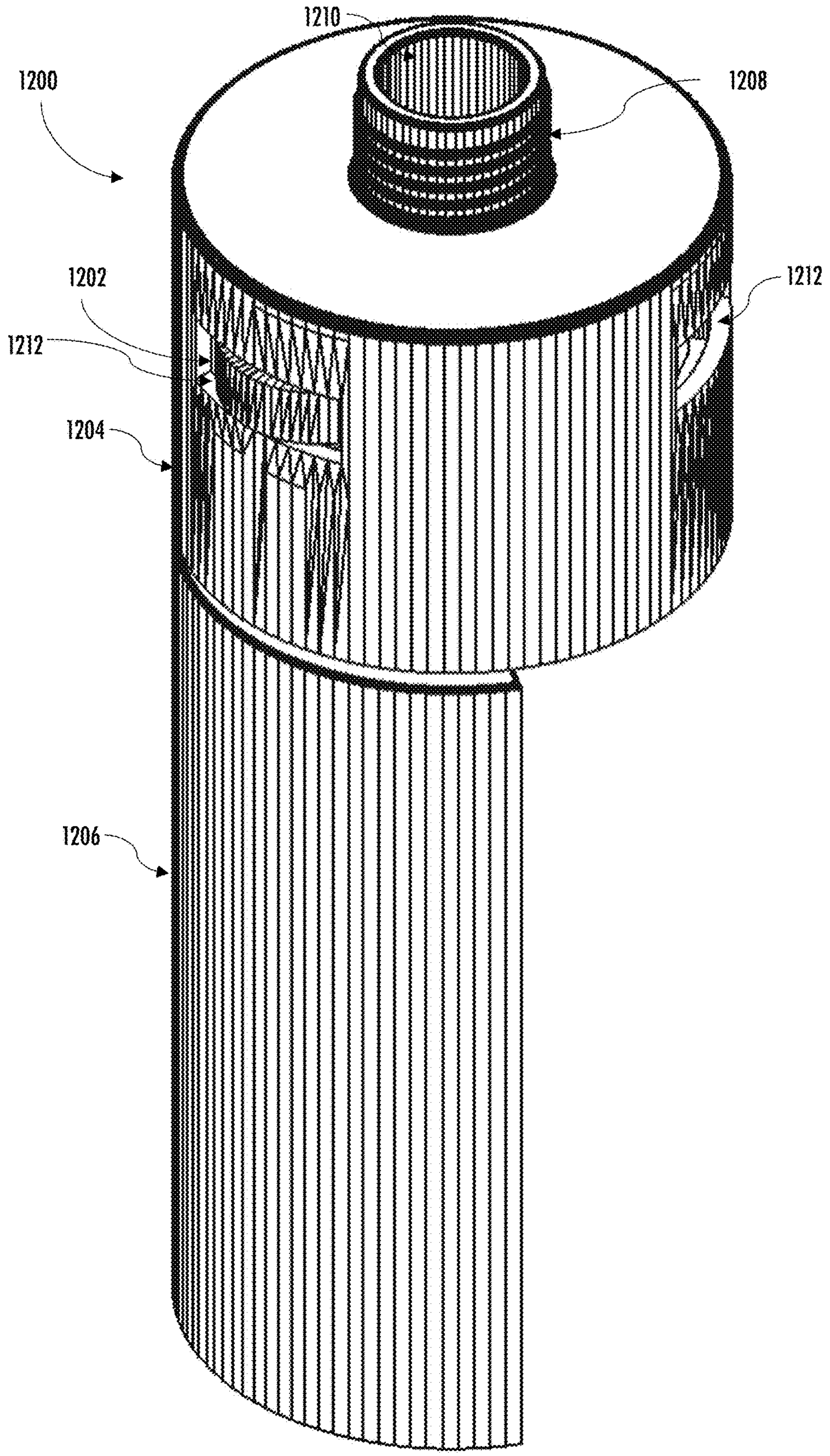
FIG. 12 is an isometric view of a portion of a fragrance dispensing device 1200 with variable control with housing, according to aspects of the present disclosure.

FIG. 12 is an isometric view of a portion of a fragrance dispensing device 1200 with variable control with housing, according to aspects of the present disclosure. Illustrated aspects of the fragrance dispensing device 1200 may be used in conjunction with features described with respect to FIG. 1. As shown in FIG. 12, the fragrance dispensing device 1200 includes variable control selector knobs 1202 partially protruding from the housing 1204. As a result, the fragrance dispensing device 1200 may have a smaller form factor than a design where dials of the variable control selector knobs 1202 are completely outside the housing 1204.

The fragrance dispensing device 1200 includes a housing 1204 and sub-containers 1206. The housing 1204 may include a housing neck 1208 that is removably coupled to a head component of a fragrance dispensing device 1200 (e.g., spray head actuator 101 within the housing component cover 102 of FIG. 1). To connect to the head component, the housing neck 1208 may be cylindrical and threaded (e.g., helical ridges or grooves) on the housing neck 1208. These threads are designed to match and engage with the corresponding threads on the head component of the fragrance dispensing device 1200 allowing the head component to be screwed on or off. An aperture 1210 at an end of the housing neck 1208 may open to an internal cavity of the housing 1204 that houses mixing components of the fragrance dispensing device 1200. Through the aperture 1210 in the housing neck 1208, a dip tube (e.g., dip tube 103) may run. The dip tube may fluidly couple the head component (including, e.g., a manual or electronically controlled pump, a spray nozzle, etc. in the head component) with components within the housing 1204 of the fragrance dispensing device 1200 (e.g., a mixing chamber). Mixed fluid (e.g., fragrance mixture, etc.) may run up the dip tube for expression from the fragrance dispensing device 1200.

The housing 1204 may be cylindrically shaped around an internal cavity with an open underside (opposite the housing neck 1208). The housing 1204 may have a larger diameter than the housing neck 1208, a flat shoulder portion of the housing 1204 may form a top side of the housing that meets the housing neck 1208. The side wall of the housing 1204 may include cutouts 1212 which the variable control selector knobs 1202 may be disposed for access and control by a user. The cutouts 1212 may allow a portion of the variable control selector knobs 1202 to protrude outside the boundaries of the cutout 1212/housing 1204.

The housing 1204 may be formed by two separate connectable portions. In one example, a first portion may include the top side of the housing including the housing neck 1208 and one half of the side wall of the housing 1204. The second portion may include the remaining side wall of the housing 1204. In some examples, one or more of the cutouts 1212 may be split between the two portions of housing.

Sub-containers 1206 may be configured to contain fluid to be mixed. As shown, the sub-containers 1206 may form a triangular prism with a rounded face. Other sub-container 1206 shapes may be used (e.g., based on the number of sub-containers 1206 in the design). For example, the sub-containers 1206 may include a rectangular/square shaped prisms. The sub-containers 1206 may have sub-containers 1206 with differing shapes or volumes to accommodate different types of liquids or container designs. The sub-containers 1206 may be removably coupled to components (e.g., a cap component) within the housing 1204 via a cylindrical sub-container neck. When installed in the fragrance dispensing device 1200, sub-containers 1206 together may form a cylindrical shape with a diameter matching the diameter of the housing 1204 (and sharing the same footprint as the housing 1204). Other footprint shapes (e.g., square/rectangular, hexagonal, octagonal) may be substituted with equal success as would be understood by artisans of ordinary skill.

The illustrated example shows a fragrance dispensing device 1200 that can mix fluid from three sub-containers 1206. Accordingly, a mixing chamber within the fragrance dispensing device 1200 may have three arms connected to three variable control selector knobs 1202 to control the amount of fluid received from the sub-containers. As would be understood by those of ordinary skill in the relevant art, other numbers of sub-containers 1206 may be used in accordance with the present disclosure. For example, the present disclosure contemplates a fragrance dispensing device 1200 with two or four (or more) sub-containers 1206 (and related components). Artisans will readily appreciate that depending on the intended number of sub-containers 1206, the number of and shape of components may differ accordingly. For example, the mixing chamber may have a greater number of few arms (attached to a greater or fewer number of variable control selector knobs 1202 in a housing 1204 with cutouts 1212 to accommodate the greater or fewer number of variable control selector knobs 1202.

Figure 13:
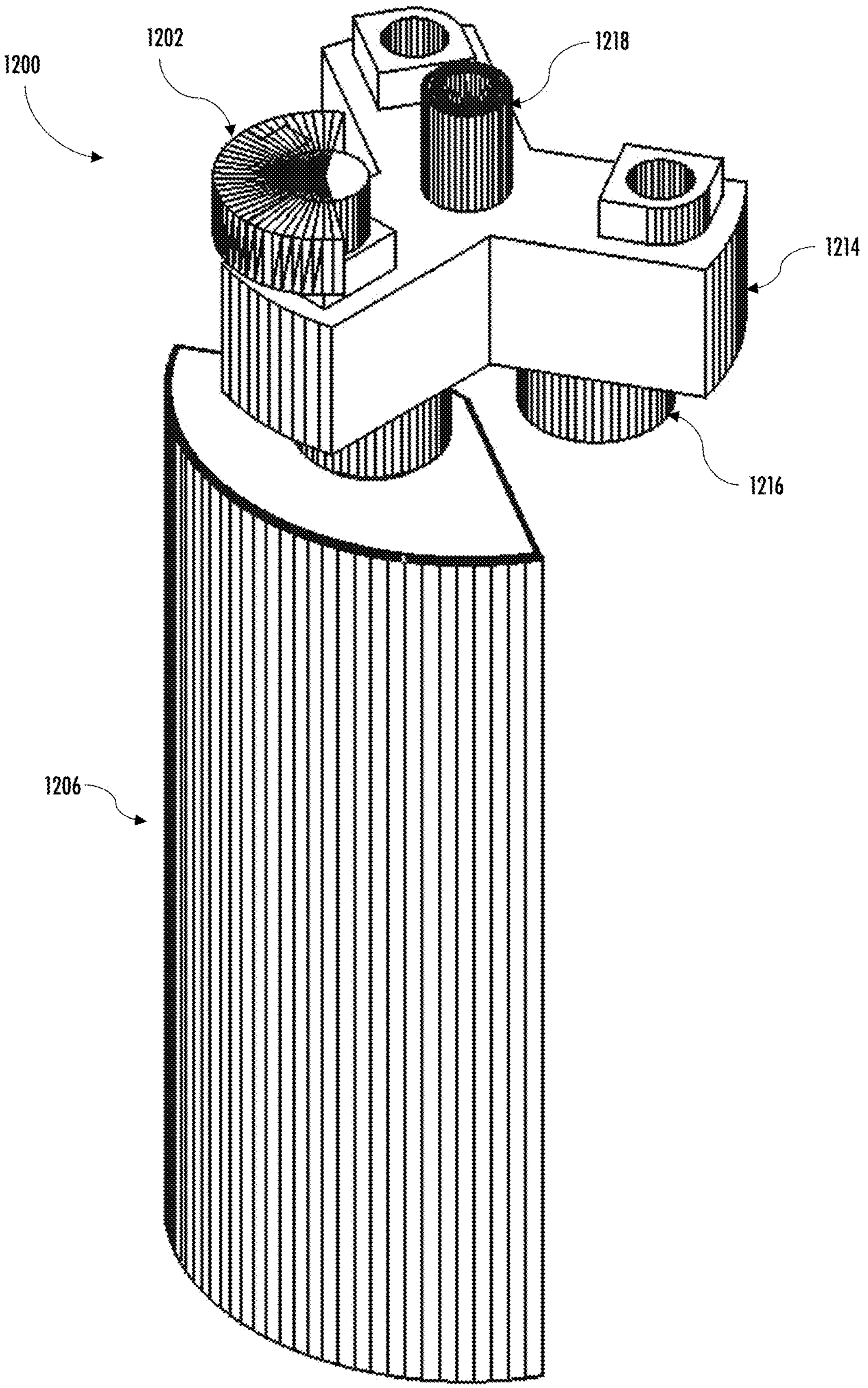
FIG. 13 is an isometric view of a portion of a fragrance dispensing device of FIG. 12 with housing 1204 removed, according to aspects of the present disclosure.

Referring also to FIG. 13, FIG. 13 is an isometric view of a portion of a fragrance dispensing device 1200 of FIG. 12 with housing 1204 removed, according to aspects of the present disclosure. Within the cavity of housing 1204 is the mixing chamber 1214. The underside of the mixing chamber 1214 is coupled to a plurality of cap-components 1216 which are removably coupled to the sub-containers 1206. In some examples, the cap-components 1216 are a single manufactured part with the mixing chamber 1214. Sub-container dip tubes coupled to the cap-components 1216 may dip into the sub-containers 1206 to draw fluid in the sub-container 1206 into the mixing chamber 1214 to mix with other fluid from the other sub-containers 1206.

A mixing chamber neck 1218 may be configured to removably enclose a portion of a dip tube that couple the head component (with a pump) to the mixing chamber 1214 and allows mixed fluid to be drawn to the pump from the sub-containers 1206. The mixing chamber neck 1218 may form a hollow cylindrical tube. The mixing chamber neck 1218 may ensure the correct placement of the dip tube when the head component is installed onto the housing 1204. When inserted into the mixing chamber neck 1218, the dip tube may form a sealed connection with the mixing chamber 1214. The sealed connection may prevent fluid from escaping out the mixing chamber neck 1218 not through the dip tube. The sealed connection may also prevent air from entering through the connection which could reduce pressure created by the pump to draw fluid from the mixing chamber 1214. In some examples, the mixing chamber neck 1218 may include a one-way valve to ensure that mixed liquid can flow up through the mixing chamber 1214 but not back down through the mixing chamber 1214 and back into the sub-containers 1206. In other examples, the mixing chamber 1214 includes one-way valve(s) where the liquid in the sub-containers 1206 mix. In some examples, the one-way valve may include a ball and spring mechanism, a flap/door style valve, etc.

Figure 14:
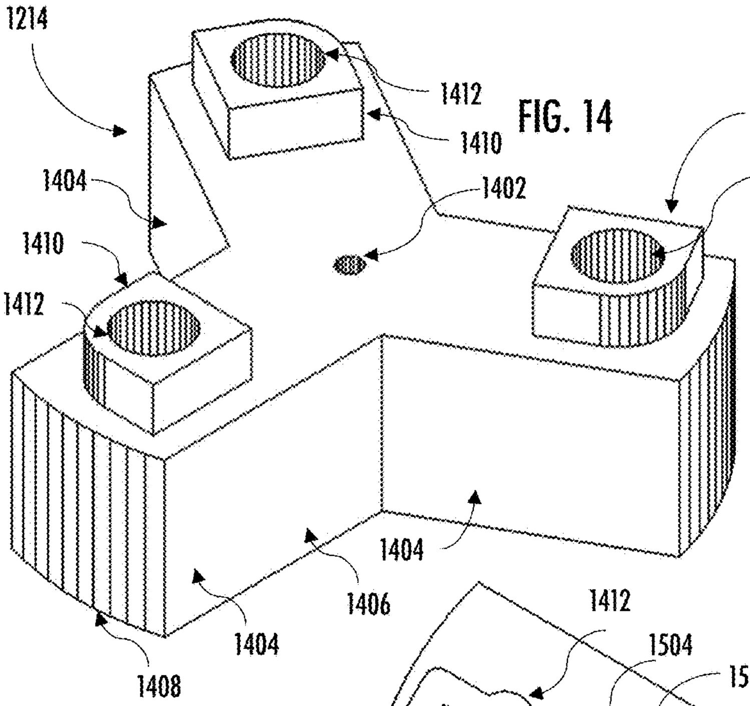
FIG. 14 is an isometric view of the mixing chamber of FIG. 12.

FIG. 14 is an isometric view of the mixing chamber 1214 of FIG. 12. As shown, the mixing chamber neck 1218 is removed to show the mixture output port 1402. The mixing chamber 1214 includes three arms 1404 that extend radially from the central portion (that includes the mixture output port 1402). In alternative embodiments, a greater or fewer number of arms 1404 may be used (e.g., two, four, etc.) and the arms 1404 may be equally spaced or variably spaced. The number of arms 1404 may correspond to the number of sub-containers 1206 connectable to the fragrance dispensing device 1200 at one time. Alternatively, the number of connectable sub-containers 1206 at one time may correspond to the number of arms 1404 of the mixing chamber 1214. In a variably-spaced embodiment, sub-containers 121 of different volumes may be used with different kinds of liquids (carrier oil/alcohol/base and fragrance concentrates) or based on a user preference (the user may install and use a larger (or smaller) sub-container of a particular preferred fragrance component).

As illustrated, each of the arms 1404 are evenly spaced (at 120 degrees apart) about the central portion of the mixing chamber 1214. In alternative examples with a greater (e.g., four or more) or fewer number (e.g., two) of arms 1404/sub-containers 1206, the arms 1404 may be spaced at other distances (e.g., 180 degrees, 90 degrees) to accommodate the difference in number. Side walls 1406 of the mixing chamber 1214 may be flat and straight. The ends 1408 of the arms 1404 of the mixing chamber 1214 may abut (and may be coupled to) an interior wall of the housing 1204. The ends 1408 of the arms 1404 may be curved to match, and conform to, the (e.g., circular/curved) curvature of the housing 1204. The arms 1404 may contain tubular passages radiating from the central portion of the mixing chamber to transport liquid.

The mixing chamber 1214 may include raised valve platforms 1410. Each raised valve platform 1410 may include a valve control aperture 1412. The valve control aperture 1412 may be couplable to a valve (e.g., the variable control selector knob 1202). A portion of a variable control selector knob 1202 may be configured to rest on a raised valve platform 1410 and another portion may fit within the valve control aperture 1412 to adjust the amount of a (pre-mixed) liquid from a sub-container 1206 that gets mixed with other liquids (from other sub-containers 1206) within the mixing chamber 1214.

Figure 15:
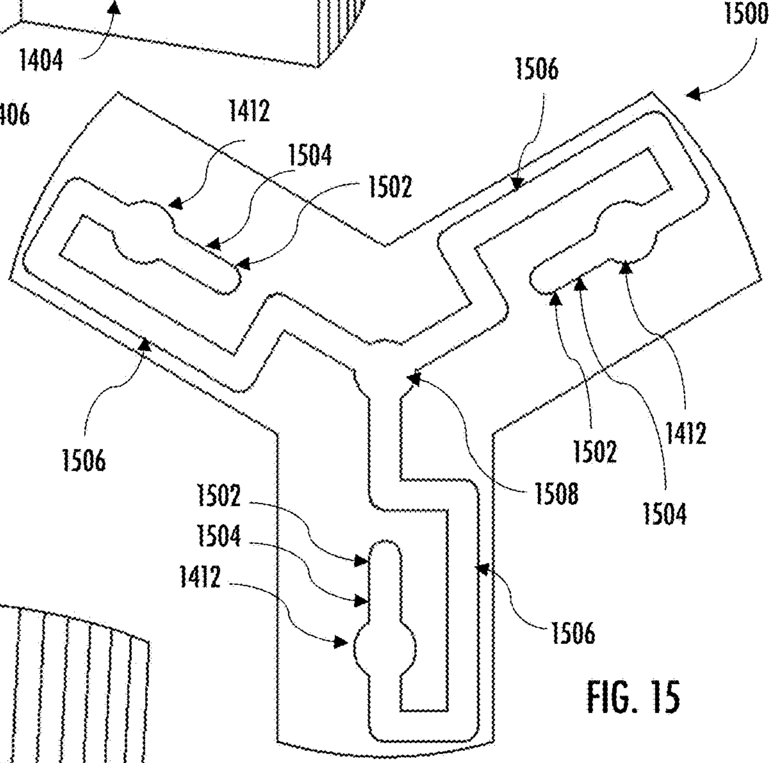
FIG. 15 is a cross-sectional view of the mixing chamber of FIG. 14.

FIG. 15 is a cross-sectional view 1500 of the mixing chamber 1214 of FIG. 14. Liquid may enter the mixing chamber 1214 via dip tubes in sub-containers 1206 coupled to cap-components 1216. The liquid may enter the mixing chamber 1214 at a mixing chamber opening 1502 at an underside of the mixing chamber 1214. The liquid may travel through a pre-valve passageway 1504 until reaching the valve control aperture 1412 with a flow control valve of the variable control selector knobs 1202. After passing through the flow control valve, liquid may travel inside a post-valve passageway 1506 towards a central passageway 1508 of the mixing chamber 1214 where the liquid from multiple sub-containers 1206 may mix before exiting the mixing chamber 1214 via the mixture output port 1402.

In some examples, the mixing chamber opening 1502, passageways 1504, 1506, and central passageway 1508 may include multiple "snake-like" turns as liquid moves from a base of the mixing chamber 1214 to the mixture output port 1402 and from the arms 1404 to the central passageway 1508 rather than take a shorter, more direct path. In these examples, the shape of the passageways 1504, 15006 may allow for alignment with the variable control selector knobs 1202 in the valve control aperture 1412. In other examples, the overall length of the passageways is minimized (e.g., without turns taking liquid to the ends of the arms 1404/performing U-turns). In other examples, passageway length may be minimized up until reaching the central passageway 1508 where the disparate liquids may mix.

Figure 16:
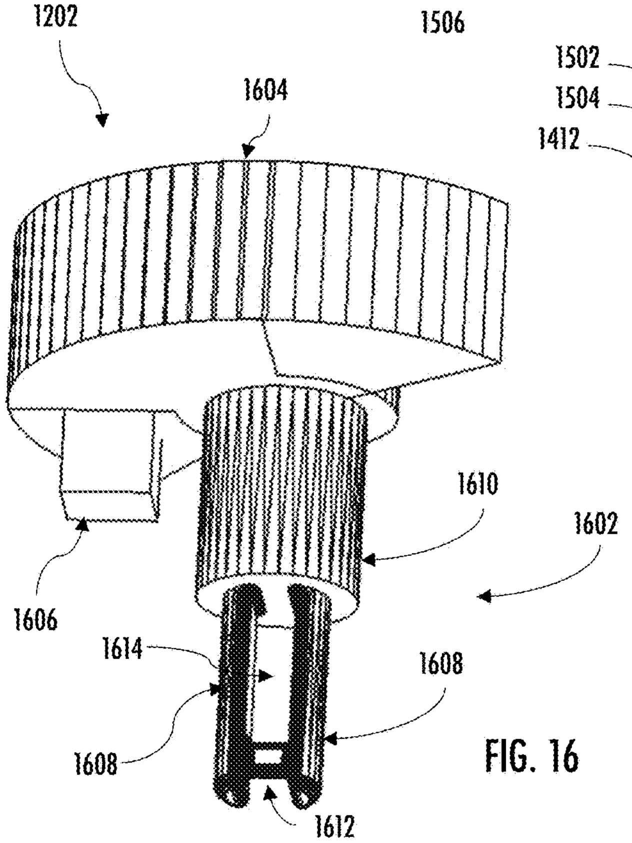
FIG. 16 is an isometric view of a variable control selector knob of FIG. 12.

FIG. 16 is an isometric view of a variable control selector knob 1202 of FIG. 12. The variable control selector knob 1202 may control the operation of a flow control valve 1602 to vary the amount of liquid able to mix in the mixing chamber 1214 of the fragrance dispensing device 1200.

The variable control selector knob 1202 includes an adjustable dial 1604. In some examples, the adjustable dial 1604 may have a face with a semi-circular shape attached to a semi-circular shape of smaller diameter (forming a circular shape with a "C"-shaped cutout). In other examples, the adjustable dial may have a circular shape. The adjustable dial 1604 configured to be adjusted by a user to adjust the flow control valve 1602. In some examples, the adjustable dial 1604 is rotatable about an axis parallel to a central axis (running top to bottom/along the length of the central passageway 1508) of the mixing chamber 1214 (and/or the longitudinal/central axis of the dip tube that connects the mixing chamber neck 1218 to the head component). The direction of rotation of the adjustable dial 1604 is orthogonal to the central axis. In some examples, when the adjustable dial 1604 is turned to the left (clockwise), the amount of liquid allowed to flow from the sub-container 1206 for blending is reduced based on a constriction of liquid flow through the passageways 1504, 1506, and 1508 in the mixing chamber 1214 by the flow control valve 1602. When the adjustable dial 1604 is turned to the right (counterclockwise), the amount of liquid allowed to flow from the sub-container 1206 for blending is expanded based on a loosening of the liquid flow through the passageways 1504, 1506, and 1508 in the mixing chamber 1214 by the flow control valve 1602.

The variable control selector knob 1202 is configured to be disposed within the valve control aperture 1412 of the mixing chamber 1214. The adjustable dial 1604 is configured to be disposed above the valve platform 1410. Said another way, the adjustable dial 1604 is configured to be on the opposite end/an opposing side of the mixing chamber from the sub-containers 1206.

Control guide projection 1606 may limit the movement of the adjustable dial 1604/variable control selector knobs 1202 to a particular range of motion. In some examples, the control guide projection 1606 may impede movement by interacting with/limited by an inner wall of the housing 1204 of the fragrance dispensing device 1200. In some examples, during rotation the control guide projection 1606 may approach and bump against the inner wall of the housing 1204. In some examples, the raised valve platform 1410 of the mixing chamber 1214 may be designed to conform to and not impede the movement/rotation of the control guide projection 1606. In other examples, the raised valve platform 1410 may limit the boundaries of motion of the control guide projection 1606 and the adjustable dial 1604/variable control selector knobs 1202 by blocking the path of rotation.

The variable control selector knobs 1202 may be disposed within the valve control aperture 1412 of the mixing chamber 1214. The post 1610 may fit and rotate within the valve control aperture 1412. The valve control aperture 1412 may have sections of varying diameter. For example, a first section of the valve control aperture 1412 may be configured to accommodate the post 1610. A second section of the valve control aperture 1412, narrower (having a smaller diameter) than the first section, may be configured to accept the valve arms 1608. While disposed within the valve control aperture 1412, the valve arms 1608 may be rotatable/controllable by a user while exerting pressure on the interior walls of the valve control aperture 1412 and/or passageways 1504 and 1506 of the mixing chamber 1214.

The variable control selector knobs 1202 adjust the amount of liquid concentrate that may flow into the mixing chamber 1214 by adjusting the position of valve arms 1608 within the mixing chamber 1214. The valve arms 1608 may be coupled to the adjustable dial 1604 by a post 1610 (adjacent to the valve arms 1608). The post 1610 may be cylindrical in shape. In some examples, the valve arms 1608 may block, restrict, impede, or allow passage of the liquid concentrate through the mixing chamber 1214. The valve arms 1608 may each be a semi-cylindrical structure (with, e.g., a half circular face) separated by a passage 1614. In some examples, the valve arms 1608 may be joined by support arms 1612. The support arms 1612 may be configured to provide structure to the valve arms 1608 to prevent the valve arms 1608 from bowing toward each other at the ends of the flow control valve 1602 opposite the post 1610. Between the valve arms 1608, a passage 1614 is formed.

In a first configuration (e.g., an open configuration) of the variable control selector knob 1202, the passage 1614 is aligned with the pre-valve passageway 1504 and the post-valve passageway 1506 forming a continuous opening, liquid may be pumped and flow from the mixing chamber opening 1502 through the mixing chamber 1214. The valve arms 1608 of the flow control valve 1602 are not blocking/impeding the flow of the liquid into the central passageway 1508 of the mixing chamber 1214.

In a second configuration (e.g., a closed configuration) of the variable control selector knob 1202, the valve arms 1608 are blocking the fluid connection between the pre-valve passageway 1504 and the post-valve passageway 1506. Liquid may not be pumped and flow from the mixing chamber opening 1502 through the mixing chamber 1214. The passage 1614 is blocked by the valve arms 1608 of the flow control valve 1602 are not blocking/impeding the flow of the liquid into the central passageway 1508 of the mixing chamber 1214. The valve arms 1608 may exert outward pressure against the sides of the pre-valve passageway 1504 (and post-valve passageway 1506) to inhibit the flow of liquid from the sub-container 1206 and pressure from the pump.

The variable control selector knob 1202 may be rotated/pivoted by a user (which rotates the flow control valve 1602). The variable control selector knob 1202 may be in the first/open configuration, the second/closed configuration, or a configuration between the first configuration and the second confirmation. In a configuration between the first configuration and the second confirmation, the valve arms 1608 may block/impede the flow of the liquid but not entirely block the fluid connection between the sub-containers 1206/pre-valve passageway 1504 and the post-valve passageway 1506/central passageway 1508 of the mixing chamber. A notation/markings on the housing 1204 and/or on the adjustable dial 1604 may indicate when the variable control selector knob 1202 is in the first configuration, the second configuration, or between the first and second configurations. The housing 1204 may include arrows indicating which direction to turn the adjustable dial 1604 of the variable control selector knob 1202 to open and/or close the flow control valve 1602.

Reference is made throughout the disclosure to top, bottom, horizontal, vertical, and 45-degree, 90-degree, and 180-degree angles and positions. These descriptors refer to the illustrated embodiments and it will be apparent to those skilled in the art after reviewing the present disclosure that other valve constructions may operate horizontally or at an angle and the vertical/horizontal valve positions may swap or other angled valve configurations may indicate "on" and "off" or that components may be flipped or rotated (such that the top is now the bottom or on the side) without a change in functionality.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A liquid dispensing apparatus, comprising:

a plurality of containers, each container of the plurality of containers configured to hold one of a plurality of liquids;

a mixing chamber comprising a plurality of valve control apertures;

a plurality of valves partially disposed within the plurality of valve control apertures, each of the plurality of valves comprising a user controllable dial coupled to the mixing chamber on an opposing side of the plurality of containers, the plurality of valves configured to control a variable amount of the plurality of liquids for mixing in the mixing chamber to create a mixed liquid; and a spray head configured to release the mixed liquid.

2. The liquid dispensing apparatus of claim 1, where each of the plurality of valves comprises valve arms disposed within the plurality of valve control apertures, the valve arms configured to control an amount of the plurality of liquids mixed in the mixing chamber.

3. The liquid dispensing apparatus of claim 2, where the user controllable dial is coupled to the valve arms.

4. The liquid dispensing apparatus of claim 1, where the user controllable dial is rotatable on an axis parallel to a central axis of the mixing chamber.

5. The liquid dispensing apparatus of claim 1, further comprising a housing with an aperture, where the user controllable dial is disposed through the aperture of the housing.

6. The liquid dispensing apparatus of claim 1, wherein at least one of the plurality of liquids comprises a fragrance, a fragrance component, a solvent, and a skincare product.

7. A liquid dispensing apparatus, comprising:

a housing;

a spray head comprising a pump;

a main dip tube coupled to the spray head, the main dip tube characterized by a longitudinal axis extending along a length of the main dip tube;

a mixing chamber coupled to the main dip tube;

a first attachable container coupled to the mixing chamber, the first attachable container configured to hold a first liquid;

a first valve coupled to the mixing chamber, the first valve comprising a first rotatable dial and configured to control a first amount of the first liquid mixed by the mixing chamber, the first rotatable dial rotatable about a first axis parallel to the longitudinal axis of the main dip tube, the first rotatable dial comprising a projection configured to interact with the housing and limit a range of motion of the first rotatable dial;

a second attachable container coupled to the mixing chamber, the second attachable container configured to hold a second liquid; and a second valve coupled to the mixing chamber, the second valve comprising a second rotatable dial and configured to control a second amount of the second liquid mixed by the mixing chamber, the second rotatable dial rotatable about a second axis parallel to the longitudinal axis of the main dip tube.

8. The liquid dispensing apparatus of claim 7, further comprising:

a first dip tube coupled to the mixing chamber and configured to be partially disposed within the first attachable container; and a second dip tube coupled to the mixing chamber and configured to be partially disposed within the second attachable container, where the pump is configured to force a first portion of the first liquid in the first attachable container through the first dip tube into the mixing chamber and a second portion of the second liquid in the second attachable container through the second dip tube into the mixing chamber to create a blended liquid based a first configuration of the first valve and a second configuration of the second valve.

9. The liquid dispensing apparatus of claim 8, further comprising a one-way valve to inhibit the blended liquid from flowing into the first attachable container and the second attachable container.

10. The liquid dispensing apparatus of claim 7, further comprising a housing encasing the mixing chamber, the housing having a first cutout providing user access to control the first rotatable dial and a second cutout providing user access to control the second rotatable dial.

11. The liquid dispensing apparatus of claim 7, where the mixing chamber has a first tubular passage and a second tubular passage radiating from a central portion, the central portion of the mixing chamber configured to receive and blend a first portion of the first liquid and a second portion of the second liquid.

12. The liquid dispensing apparatus of claim 7, further comprising:

a third attachable container coupled to the mixing chamber, the third attachable container configured to hold a third liquid; and a third valve coupled to the mixing chamber, the third valve comprising a third rotatable dial and configured to control a third amount of the first liquid mixed by the mixing chamber, the third rotatable dial rotatable about a third axis parallel to the longitudinal axis of the main dip tube.

13. The liquid dispensing apparatus of claim 7, where:

the first valve comprises first valve arms, the second valve comprises second valve arms, and the mixing chamber comprises a first valve control aperture and a second valve control aperture, the first valve arms disposed within the first valve control aperture and the second valve arms disposed within the second valve control aperture.

14. The liquid dispensing apparatus of claim 13, where:

the mixing chamber comprises a first pre-valve passageway, a first post-valve passageway, a second pre-valve passageway, and a second post-valve passageway, the first pre-valve passageway and the first post-valve passageway are separated by the first valve control aperture, the first valve arms configured to inhibit the first liquid from passing between the first pre-valve passageway and the first post-valve passageway, the second pre-valve passageway and the second post-valve passageway are separated by the second valve control aperture, and the second valve arms configured to inhibit the second liquid from passing between the second pre-valve passageway and second first post-valve passageway.

15. An apparatus for mixing liquid, comprising:

a central portion comprising a central cavity connected a first aperture on a first end of the apparatus for mixing liquid; and a plurality of lateral arms extending from the central portion, wherein each of the plurality of lateral arms comprise:

a second aperture disposed on a second end of the apparatus for mixing liquid;

a pre-valve lateral arm cavity fluidly coupled to the second aperture;

a post-valve lateral arm cavity fluidly coupled to the central cavity; and a valve cavity on the first end of the apparatus for mixing liquid, the valve cavity couplable to a valve configured to control a flow of liquid between the pre-valve lateral arm cavity and the post-valve lateral arm cavity.

16. The apparatus for mixing liquid of claim 15, where the valve cavity fluidly couples the pre-valve lateral arm cavity and the post-valve lateral arm cavity.

17. The apparatus for mixing liquid of claim 15, where the valve cavity is characterized by a cylindrical portion adjacent to the pre-valve lateral arm cavity and the post-valve lateral arm cavity, the cylindrical portion of the valve cavity characterized by a first diameter larger than a cross-section of the pre-valve lateral arm cavity.

18. The apparatus for mixing liquid of claim 17, where:

the first diameter is configured to accommodate valve arms of the valve, the valve arms are separated by a valve arm passage, the valve configured to be rotated in the valve cavity between an open configuration and a closed configuration, in the closed configuration, at least one of the valve arms blocks fluid coupling between the pre-valve lateral arm cavity and the valve cavity, and in the open configuration, the valve arm passage fluidly couples the pre-valve lateral arm cavity and the post-valve lateral arm cavity.

* * * * *